United States Patent [19]

Siler-Khodr

[11] Patent Number: 5,168,061
[45] Date of Patent: Dec. 1, 1992

[54] HUMAN CHORIONIC PEPTIDASE-1

[75] Inventor: Theresa M. Siler-Khodr, San Antonio, Tex.

[73] Assignee: Board of Regents, The University of Texas System, Austin, Tex.

[21] Appl. No.: 323,325

[22] Filed: Mar. 14, 1989

Related U.S. Application Data

[63] Continuation-in-part of Ser. No. 863,310, May 15, 1986, Pat. No. 4,945,055.

[51] Int. Cl.$^5$ .................... A61K 37/54; C12N 9/48; C12N 9/50; C12N 9/64
[52] U.S. Cl. ................................ 435/219; 435/212; 435/226; 435/183; 424/94.63
[58] Field of Search ............... 435/226, 219, 212, 183; 424/94.63

[56] References Cited

U.S. PATENT DOCUMENTS

| | | | |
|---|---|---|---|
| 4,338,305 | 7/1982 | Corbin | 424/177 |
| 4,621,055 | 11/1986 | Theurer | 435/69 |
| 4,622,218 | 10/1986 | Bodor | 424/9 |
| 4,732,763 | 3/1988 | Beck et al. | 424/433 |
| 4,756,907 | 7/1988 | Beck et al. | 424/85 |
| 4,945,055 | 7/1990 | Kuehl et al. | 435/226 |

FOREIGN PATENT DOCUMENTS

| | | | |
|---|---|---|---|
| 57-74087 | 5/1982 | Japan | 435/226 |
| 58-36387 | 3/1983 | Japan | 435/212 |

OTHER PUBLICATIONS

Mentlien et al., Chem. Abstr. 15, 122, 831V, 1982.
Johnson et al., Chem. Abst. 21, 188, 645V, 1984
Pueschel et al. Chem. Abstr. 17, 140, 765f, 1982.
Suzuki, Biosis Abst., 81,022,408, 1985.
Mitzutani et al., Chem. Abst. 5, 33,917c, 1985.
Hersh et al., "Enzymes Involved in the Degradation of Thyrotropin Releasing Hormone (TRH) and Luteinizing Hormone Releasing Hormone (LH-RH) in Bovine Brain", (1979) Brain Research, 168: 553-564.
Chertow, "The Role of Lysosomes and Proteases in Hormone Secretion and Degradation", (1981) Endocrine Reviews, 2 (2): 137-173.
Mizutani et al., "Post-Proline Endopeptidase in Human Placenta", (1984) Biochemica et Biophysica Acta, 786: 113-117.
Johnson et al., "Enzymes in Placental Microvilli: Angiotensin I Converting Enzyme, Angiotensinase A, Carboxypeptidase, and Neutral Endopeptidase (Enkephalinase)", (1984) Peptides, 5(4): 789-796.

(List continued on next page.)

Primary Examiner—David M. Naff
Assistant Examiner—Mike Meller
Attorney, Agent, or Firm—Arnold, White & Durkee

[57] ABSTRACT

A chorionic peptidase-1 (C-ase-1) which is isolated from human placenta that inactivates the immunoreactivity of GnRH, TRH and angiotension II. Only in the presence of dithiothreitol (DDT), a sulfhydryl agent, are oxytocin and somatostatin inactivated by this peptidase. However, C-ase-1 is without effect on CRF, hCS or hCG. C-ase-1 also inhibits the biological activity of GnRH, i.e. its ability to stimulate pituitary LH and FSH. The ability of this peptidase to inactivate GnRH, TRH and angiotension II can be inhibited by various peptidase inhibitors. These peptidase inhibitors include bacitracin, para-amino bensamidine, DMSO and diisopropylfluorophosphate. The activity of C-ase-1 in GnRH has also been demonstrated to be a post-proline peptidase.

Isolation of this protein, C-ase-1, has been effected using permeation, ion exchange and affinity chromatography and HPLC. As estimated by SDS-PAGE and HPLC analysis, C-ase-1 has an apparent molecular weight of about 58,000 daltons. It is proposed that C-ase-1 may be an important chorionic regulator of GnRH, TRH and angiotension II levels during pregnancy.

12 Claims, 13 Drawing Sheets

OTHER PUBLICATIONS

Kenny et al., "Dipeptidyl Peptidase IV, a Kidney Brush-Border Serine Peptidase", (1976) Biochem. J., 155: 169–182.
Kang et al., Society for Gynecological Investigation (Mar. 15, 1989).
Kang et al., The Endocrine Society (Jun. 1989).
Seeburg et al., Nature, 311:666 (1984).
Lee et al., Acta Endocrinol., 96:394 (1981).
Tan et al., Biochem. Biophys. Res. Commun., 109:1061 (1982).
Siler-Khodr et al., Life Sci., 32:2742 (1983).
Siler-Kodhr et al., Fertil. Steril., 41:448 (1984).
Gibbons et al., Am. J. Obstet. Gynecol., 121:127 (1975).
Siler-Khodr and Khodr, Am. J. Obstet. Gynecol., 130:216 (1978).
Siler-Khodr and Khodr, Fertil. Steril., 32:294 (1979).
Siler-Khodr et al., Am. J. Obstet. Gynecol., 150:376 (1984).
Khodr and Siler-Khodr, Fertil. Steril., 2:523 (1978).
Seppala et al., Clinical Endocrinol., 12:441 (1980).
Miyake et al., Obstet. Gunecol., 60:444 (1982).
Khodr and Siler-Khodr, Fertil. Steril., 30:301 (1978).
Siler-Khodr and Khodr, Biol. Reprod. 25:353 (1981).
Khodr and Siler-Khodr, Science, 207:315 (1980).
Siler-Khodr and Khodr, Fetal Endocrinology, Novy, Rosko, Ed., Academic Press, New York, p. 183 (1981).
Siler-Khodr and Khodr, in Role of Peptides and Proteins in Control of Reproduction, Dhindsa McCann, Ed. Elsevier North Holland, New York, p. 347 (1982).
Siler-Khodr, Clinics in Perinator., 10:553 (1983).
Siler-Khodr, Sem. in Reproduct. Endocrinol., 1:321 (1983).
Siler-Khodr and Khodr, Endocrinology, 56:274 (Abstract #776) (1983).
Siler-Khodr et al., Scientific Program and Abstracts of the 31st Annual Meeting of the Society for Gynologic Investigation, San Francisco, Calif., Abstract No. 316:190 (1984).
Siler-Khodr et al., the 32nd Annual Meeting of the Society for Gyncologic Investigation, Phoenix, Ariz. (1985).
Poisner et al., Federation Proceedings Abstract No. 1003, p. 326 (1986).
Gautron et al., Molec. Cell. Endocr., 24:1 (1981).
Seppala et al., Life Sciences, 25:1489 (1979).
Seppala et al., Life Sciences, 27:395 (1980).
Seppala and Wahlstrom, Int. J. Cancer, 26:267 (1980).
Eidne et al., Science, 229989 (1985).
Dutlow and Miller, Biochem. Biophys. Res. Commun. 101:486 (1981).
Bhasin et al., Endocrinol., 112:1144 (1983).
Sokol et al., Biol. of Reprod. vol. 33, 370, (1985).

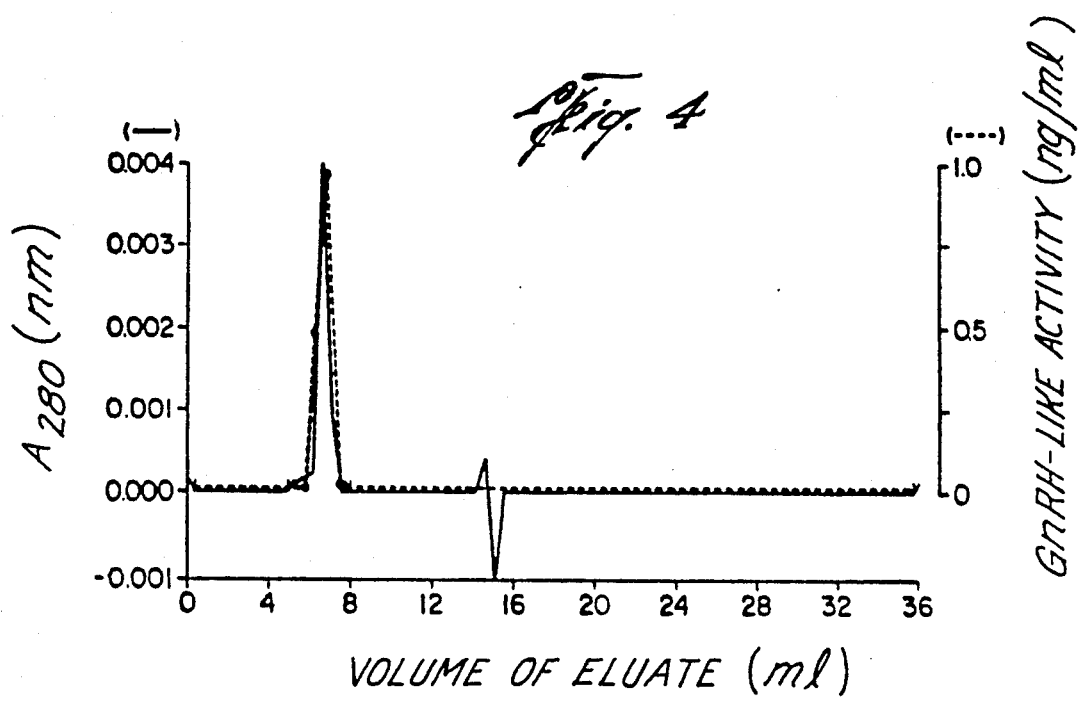
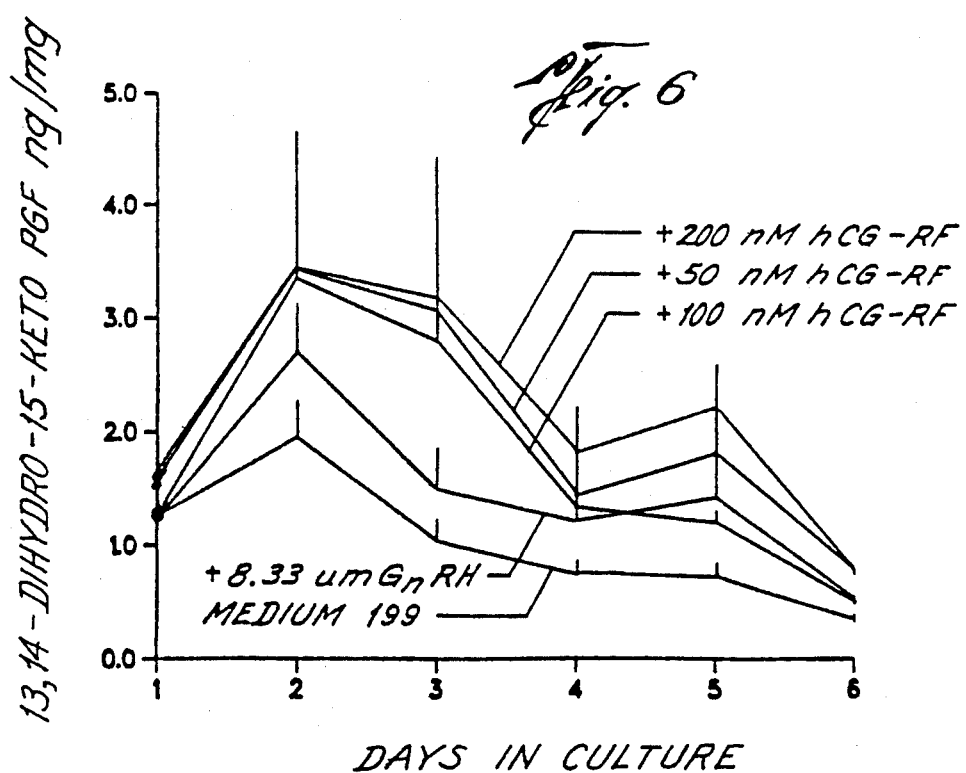

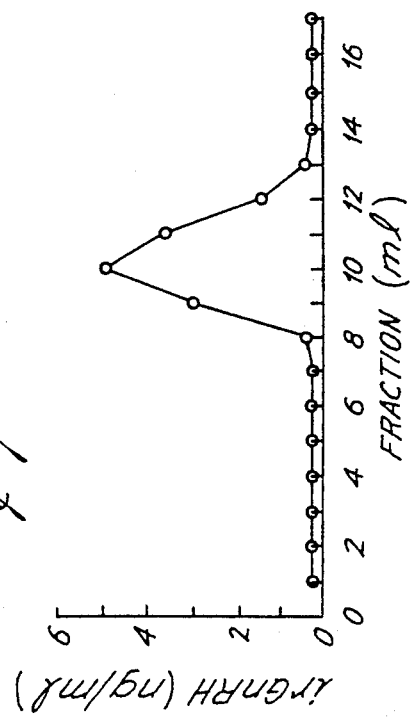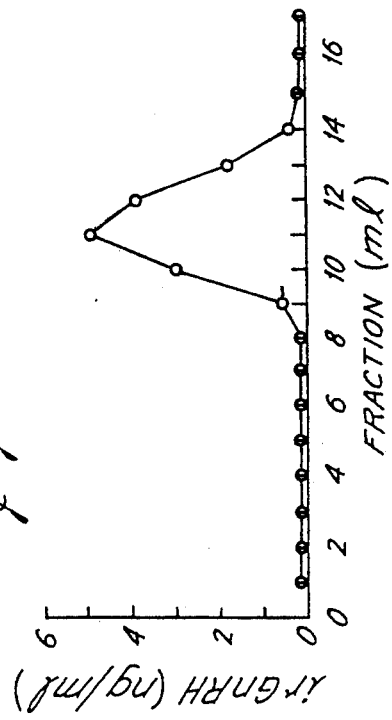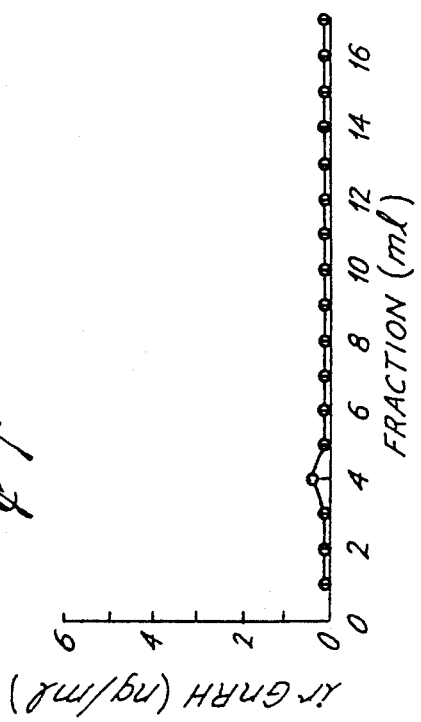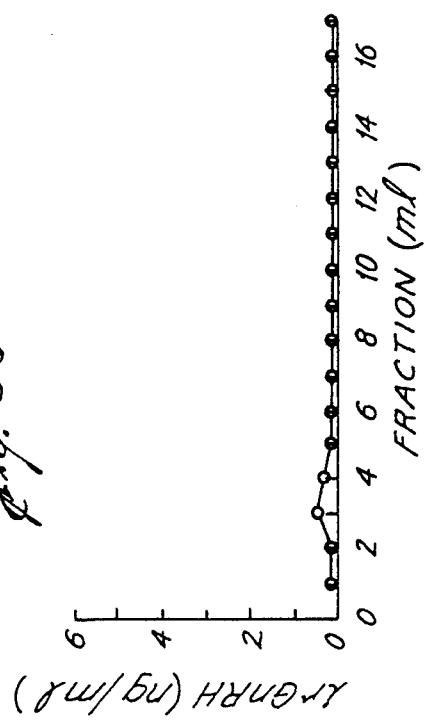

HUMAN CHORIONIC PEPTIDASE-1

The U.S. government may have rights concerning the present invention because relevant developmental work was supported by NIH grant No. HD 14842.

Specific reference is hereby made to U.S. Ser. No. 863,310, filed May 15, 1986, now U.S. Pat. No. 4,945,055 of which the present application is a continuation in part. U.S. Pat. No. 4,945,055 is also expressly incorporated by reference in the present application.

BACKGROUND OF THE INVENTION

The present invention is related to a newly discovered and isolated human chorionic peptidase (C-ase-1) and its uses, such as affecting states of pregnancy and as a drug screening tool.

Gonadotropin releasing hormone-like material has been identified in various biological fluids and tissues such as hypothalami, semen, testes, placenta, pancreas and mammary carcinoma. It is generally believed that gonadotropin releasing hormone (GnRH) is identical or similar to luteinizing hormone releasing factor (LRF) and is a small peptide. This small peptide is generally agreed to be a decapeptide with the amino acid sequence: pyro-glu-his-trp-ser-tyr-gly-leu-arg-pro-gly-NH$_2$. GnRH-like material appears to be synthesized by placenta and numerous other tissues and to have receptor sites in diverse organs. The present invention describes a novel protein, a human chorionic peptidase enzyme (C-ase-1) which has never before been identified and is completely unique in many ways from GnRH. Antibodies directed toward GnRH have indicated the presence of GnRH-like material at numerous other biological sites. A 92 amino acid peptide has been reported which contains the decapeptide GnRH (Seeburg et al., (1984) *Nature*, 311:666), but the human chorionic peptidase (C-ase-1) described herein differs from it.

Earlier studies by Siler-Khodr et al. ((1982) *Science*, 207:315) and others have demonstrated that an immunologically and biologically active GnRH was synthesized and released from human placental extracts. This GnRH eluted from CM-cellulose in the same area as synthetic GnRH. In addition, Lee at al. (1981) (*Acta Endocrinol.*, 96:394) reported an apparent GnRH immunoreactivity from acid extracts of placentas that eluted on HPLC in the area of GnRH. These findings led to the hypothesis that placental apparent GnRH immunoreactivity and synthetic GnRH were chemically similar. Additionally, Tan et al. (1982) (*Biochem Biophys. Res. Commun.*, 109:106 1) reported that the GnRH decapeptide sequence was present in the acid extracts of placenta. More recently, Seeburg et al. (1984) (*Nature*, 311:666), using cDNA expression, deciphered an mRNA coding for 92 amino acids in which the GnRH sequence was contained.

Certainly, the presence of the decapeptide GnRH in the placenta has been firmly supported. The role of GnRH in placental endocrinology has not been answered by the above cited studies. It has been demonstrated that synthetic GnRH can affect placental hormonogenesis, yet high concentrations are needed. An antagonist of GnRH has been shown to inhibit placental hormonogenesis both in vitro (Siler-Khodr et al., (1983) *Life Sci.*, 32:2742) and in vivo (Siler-Khord et al., (1984) *Fertil-Steril*, 41:448). Other studies have demonstrated that a placental receptor recognizes synthetic GnRH; however, the dissociation constant of the placental receptor for synthetic GnRH was found to be only $10^{-7}$M, and a potent agonist of GnRH on the pituitary had no greater affinity for this placental receptor than did GnRH. Thus, it appeared that the placental receptor recognizing synthetic GnRH differed from the pituitary receptor. The inventor has also noted that, although there was newly synthesized apparent GnRH immunoreactivity recovered in the GnRH area following CM cellulose chromatography, it accounted for only <1% of the apparent GnRH immunoreactivity. In addition, as reported herein, it was observed that apparent GnRH immunoreactivity of the placenta was extracted with a very low yield with methods typically utilized for extraction of hypothalamic GnRH, i.e. acid or methanol.

Applicant was able to extract from human placenta with an aqueous neutral buffer a substantially purified preparation of a chorionic protein with apparant GnRH-immunoreactivity and prostaglandin and hCG-releasing activity, and characterized it as a large molecular weight glycoprotein, having a molecular weight of between about 50,000 and about 70,000 daltons. It was found that this factor possessed the ability to inactivate GnRH. However, this preparation was purified only about 10% from crude placental extracts. Additionally, the mechanism by which the factors apparent immunoreactivity to GnRH was not known. It was hypothesized that the factors apparent immunoreactivity to GnRH was either a function of the factors immunological competition with or direct alteration of GnRH. This alteration was thought to be due to a hydrolytic degradation or some other unspecified activity. These findings led the inventors to consider whether this factor could be used to specifically regulate the synthesis, release, and metabolism of the myriad of hypothylamic-like releasing/inhibiting hormones produced by or circulating in the human placenta (i.e., GnRH, angiotensin II, TRH, somatostatin). Further, it was also speculated that the specificity of the factors action could be more closely regulated in vivo if the factor were further purified and specific enzyme inhibitors thereto characterized.

As with any partially purified preparation, the possibility that the crude preparation would elicit an antigenic response in the treated animal existed. Additionally, such a risk was amplified by the relatively low level of purification obtained in prior preparations, thus requiring large amounts of the impure preparation be administered in order to achieve desired doses of the "factor". Moreover, the elucidation of the mechanisms by which the active ingredient precipitated the degradation of GnRH and other factors would allow for the selection and use of the most effective enzyme analogues to control chorionic GnRH, as well as other factors' activity at the placental level. Such information would also serve in the regulation of other chorionic tissues where GnRH acts in a paracrine fashion to regulate hormonal functions during pregnancy. Thus, the further characterization and purification of a placental enzyme isolate which was non-antigenic to the host, possessed high specific activity and which specifically inhibited peptides used clinically during pregnancy would be a significant step forward in the medical science of animal reproduction and growth.

The following comprises a list of abbreviated terms as used throughout the present application.

C-ase-1—chorionic peptidase one.

OXY—oxytocin.
TRH—thyrotropin-releasing factor.
GnRH—gonadotropin-releasing hormone.
irGnRH—immunoreactive gonadotropin-releasing hormone.
hCGRF—human chorionic gonadotropin-releasing factor.
DTT—dithiothreitol.
CRF—corticotropin-releasing factor.
Try-CRF—tryptophan corticotropin-releasing factor.
LH—luteinizing hormone.
rLH—rat luteinizing hormone.
FSH—follicle stimulating hormone.
rFSH—rat follicle stimulating hormone.
LRF—luteinizing hormone-releasing factor.
EDTA—ethylenediaminetetraacetic acid.
hCG—human chorionic gonadotropin.
hCS—human chorionic somatomammotrophin.
BSA—bovine serum albumin.
PGE—prostaglandin E.
MPF—metabolite prostaglandin $F_2$ alpha;
SRIF—somatotropin release-inhibiting factor; somatostatin.
Try-SRIF—tryptophan somatotropin release-inhibiting factor.
MSH—melanocyte-stimulating hormone.

SUMMARY OF THE INVENTION

The present invention broadly comprises an isolated human chorionic enzyme, chorionic peptidase one (C-ase-1) which is a glycoprotein with a molecular weight of about 58,000 daltons, and methods of using this peptidase to affect pregnancy. Also included is a method of isolating this peptidase from human placental tissue. This C-ase-1 has been shown to inactivate angiotensin II, GnRH and TRH. This GnRH degradative activity has also been shown to be reversed by a class of peptidase inhibitors, including bacitracin, para-aminobenzamidine, di-isopropylfluoro-phosphate and DMSO. Other peptidase inhibitors have no affect on the degradative-GnRH ability of C-ase-1, including alpha-1-anti-trypsin, 2-nitro-4-carboxyphenyl, N,N,-diphenyl-carbamate, pepstatin, EDTA, amastatin, bestatin, leupeptin and aprotinin.

The presently described C-ase-1 enzyme has a site-specific cleavage action which makes the enzyme incapable of cleaving peptides with disulphide bonds, such as oxytocin and somatostatin. However, the addition of a sulfhydral agent, such as dithiothreitol (DTT), allows for the degradation of somatostatin and oxytocin. Bacitracin has been shown to inhibit C-ase-1 degradation of GnRH, TRH, and angiotensin II, and also to inhibit the peptidase action on oxytocin and somatostatin in the presence of DTT.

All the peptides which were most actively degraded by C-ase-1 contained a prolein (PRO) residue, where it is proposed these peptides are cleaved by C-ase-1. This PRO residue in oxytocin (OXY) is only assessible after breaking the disulfide bond, thus DTT makes oxytocin suspectible to rapid degradation of C-ase-1. Larger peptides, or peptides without PRO such as CRF, are not inactivated by C-ase-1. In addition, larger proteins such as hCG, hCS, are not effected by C-ase-1.

The peptidase has been isolated free of GnRH and has a specific activity of about 1.2 microgram apparent irGnRH per milligram protein, thus possessing more than a 10-fold increase in specific activity over other proposed placental proteins. This peptidase has also been isolated essentially free of other impurities, including albumin, making it a more desirable therapeutic tool in the clinical setting.

The present invention also includes a method for extracting C-ase-1 peptidase from preparations of human placental tissue, and uses thereof.

BRIEF DESCRIPTION OF THE DRAWINGS

FIG. 4 describes the chromatogram (A280 nm) following HPLC of chorionic C-ase-1 on a permeation column, BioRad TSK-250, in 0.01M DTT (pH 7.2) with a flow rate of 1.0 ml per min as shown. The second reading at 14–15 min was due to glycerol added to the sample prior to storage at −20° C. The chorionic C-ase-1 activity (o---o) eluted at 6.5 to 7.0 min as did the protein peak. Using the same solvent system, synthetic GnRH eluted at 22–25.5 min.

FIG. 6 describes the release of 13,14-dihydro-15-keto prostaglandin (ng/mg placental tissue, mean ±SEM) from human term placental cultures incubated in Medium 199, Medium 199 with 8.33 uM GnRH, and Medium 199 with hCG-RF (50.0 nM, 100 nM and 200 nM). The hCG-RF-containing media was spiked on days 5 and 6 with additional 14.6, 29.2, 43.7 nM hCG-RF respectively.

FIG. 9 describes the recovery of GnRH after incubation (24 h at 4° C.) with chorionic C-ase-1, shown at (A), and can be compared to that when incubated with the heated enzyme shown at (B). Control incubates of enzyme only shown at (C), or GnRH only shown at (D), are shown in the lower graph. When bromophenol blue areas were aligned, the GnRH peaks were essentially identical in the incubates having GnRH plus heated chorionic C-ase-1, shown at (B), or only GnRH, shown at (D).

DESCRIPTION OF PREFERRED EMBODIMENTS

Figure 1:
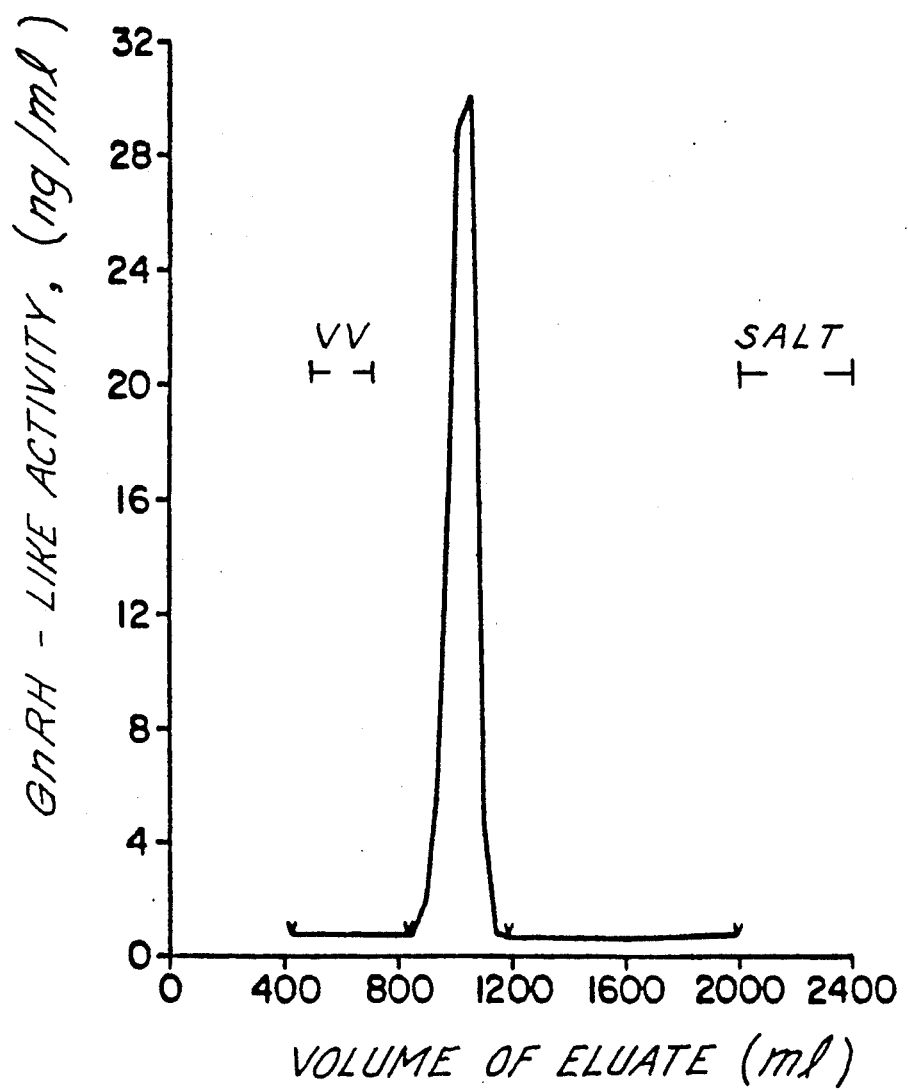
FIG. 1 describes the elution of C-ase-1, as determined from a Sephadex G 150 column (5×90 cm in 0.01M Tris, 0.001M DTT, 0.0004% pepstatin, pH 7.0). Synthetic GnRH eluted in the salt area and BSA in the peak area.
Figure 3:
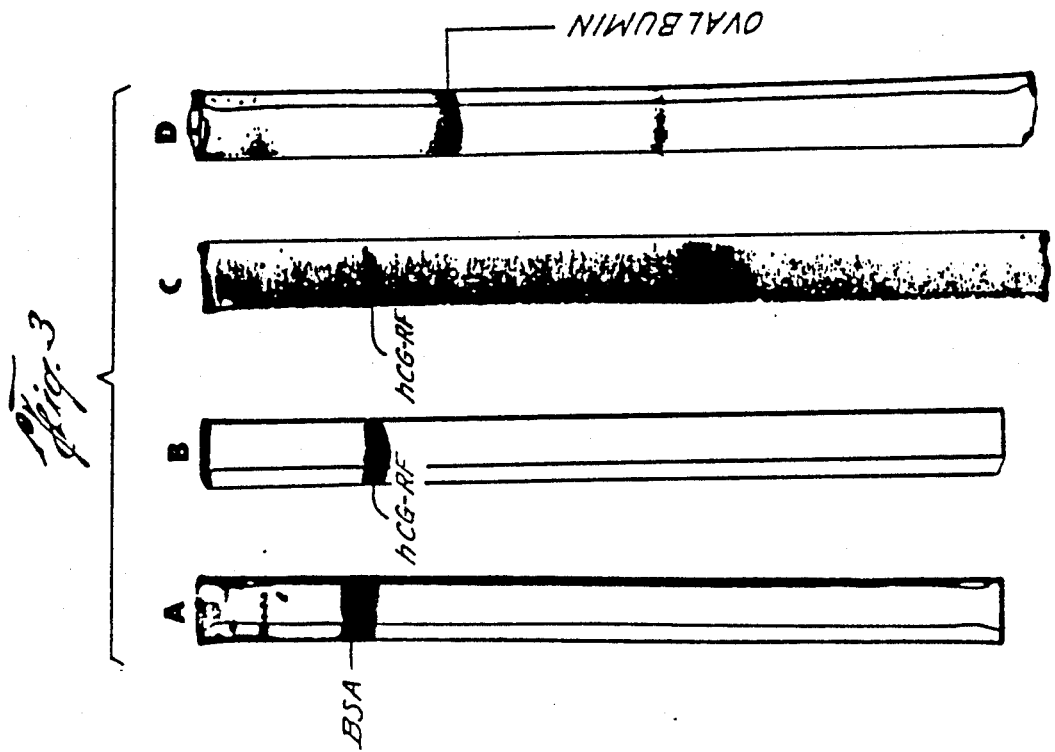
FIG. 3 describes PAGE gels for a) BSA, b) hCG-RF, c) hCG-RF and d) ovalbumin. Gels a and b were stained with Coomassie Brilliant Blue for protein and gels c and d with Schiff's periodate stain for sugars. The second band on the lower part of the c and d gels was due to the 15% sucrose added to the sample for ease of application.

A placental peptidase enzyme which degrades TRH, angiotensin II and GnRH has been isolated, essentially free of albumin and other contaminants, as an isolate from a 40,000-fold purified preparation of human placental tissue. This endogenous C-ase-1 peptidase has an apparent molecular weight of about 60,000 daltons, as estimated by SDS-PAGE and HPLC analysis. The peptidase may be used in very small doses clinically to affect pregnancy by stimulating the release of hCG, prostaglandins and other regulatory hormones without the danger of invoking an immune response in the recipient. For example, as little as 65 nM of this purified isolate has been shown to stimulate placental hCG, PGE, and MPF release with a potency much greater than that of GnRH, i.e. 230, 600, and 600 times, respectively. This C-ase-1 had a much greater bioactivity on these placental hormone release than did the decapeptide, GnRH.

Additionally, the enzyme is characterized by specific inhibitors, which add to the desirability of its clinical use. For example, the enzymes' ability to inactivate GnRH has been shown to be inhibited by various peptide inhibitors, including bacitracin, diisopropylfluorophosphate, DMSO, pepstatin and paraaminobenzamidine (PAB). Results obtained in these inhibition studies are shown in Table 1. This enzyme has been further characterized as a site-specific peptidase, lacking the ability to enzymatically degrade disulfide bonds or larger peptides or proteins such as hCG.

TABLE 1

| Effect of Various Peptidase Inhibitors on the GnRH-Degrading Activity of C-ase-1 | | |
|---|---|---|
| Inhibitor | Concentration | % GnRH Recovered |
| Tris-DTT | 10 mM, 1 mM | 0.04% |
| Diisopropylfluoro-phosphate | 1 mM | 111 |
| PAB | 25 mM | 112 |
| Bacitracin | 446 U/ml | 107 |
| DMSO | 2% | 93.1 |
| Pepstatin | 0.01% | 0.04 |
| a-1-antitrypsin | 10 mg | <0.02 |
| 2-Nitro-4-Carboxyl-phenyl, N,N-Diphenyl-Carbamate | 73.3 ug/ml | 0.02 |
| Amastatin | 10 ug/ml | 0.01 |

TABLE 1-continued

| Effect of Various Peptidase Inhibitors on the GnRH-Degrading Activity of C-ase-1 | | |
|---|---|---|
| Inhibitor | Concentration | % GnRH Recovered |
| Bestatin | 10 ug/ml | 0.01 |
| Leupetin | 20 ug/ml | 0.01 |
| Aprotinin | 0.13 TIU/ml | 0.01 |

The following examples are presented to illustrate preferred embodiments of the present invention and to be enabling descriptions. These examples are not meant to limit the claims of the patent unless otherwise specifically so stated in these claims. Examples 1-7 illustrate materials and methods applicable to the present invention. Examples 8-15 illustrate results accomplished and proposed uses of the present invention.

EXAMPLE 1

Placental Extractions

Human placentas were obtained following normal term deliveries from patients admitted to the Obstetrics Unit of the Medical Center Hospital (San Antonio, Tex.). Placental tissue was devascularized free of membranes and vessels, cut into large pieces, rinsed of excess blood in normal saline and then lyophilized. The lyophilized tissue was then pulverized and extracted. Extraction of individual lyophilized, pulverized term placenta was done at room temperature, beginning with two acetone washes (1000 ml each). This initial step defatted the tissue and removed GnRH (99.9%) without extracting the C-ase-1, and was followed by extraction of the C-ase-1 from the acetone precipitate with 300 ml of 0.01M Tris, 1 mM ditheothreitol (DTT) and 0.0004% pepstatin buffer (Tris-DTT-pepstatin). Pepstatin was included in the buffer to preserve the C-ase-1 during storage and purification, and DTT to prevent aggregation of the C-ase-1. The placental suspension was centrifuged at 4° C., 3000×g for 30 min and the supernatant (total volume, 160 ml) was used in the following characterization studies.

The total C-ase-1 recovered with this extraction method was quantitated in the GnRH radioimmunoassay (RIA) obtained using aliquants of ≦10 ul (microliter) of the resultant extract. The C-ase-1 activity recovered was quantitated by determining the inhibition of $^{125}$I-GnRH binding (due to its degradation) to antibody in he GnRH-RIA; thus, the concentration of C-ase-1 produced an apparent GnRH immunoreactivity (apparent irGnRH).

In this method, 100 ul (microliter) antiserum (final dilution of 1/300,00) was mixed with 20 pg of $^{125}$I-GnRH and C-ase-1 (≦10 ul [microliter]) or standard GnRH in a total volume of 500 ul (microliters) buffer. Incubation was for 20 hours at 4° C. The antibody-bound$^{125}$I-GnRH was separated and counted.

EXAMPLE 2

Initial Characterization of C-ase-1 Activity

Freeze-dried term placentas were extracted with 10 mM Tris, 1 mM dithiothreitol and 0.0004% pepstatin, pH 7.2 (Tris-DTT-pepstatin buffer, 300 ml per placenta). Other buffers effective at about this pH and certain other protease inhibitors or sulfhydryl compounds should give equally satisfactory results. Following centrifugation of the 3,000×g supernatant at 4,000×g for 30 min. at 4° C., various studies were performed as follows.

(1) Differential Centrifugation

The solubility of the apparent GnRH immunoreactivity in the placental extract was monitored before and after differential centrifugation. The supernatant and precipitate (resuspended in distilled water) from the placental extracts following centrifugation at 4° C., 4,000×g was determined (Table 2). This supernatant was again centrifuged at 10,000×g and aliquants of the resulting supernatant and precipitate assessed for C-ase-1 activity. The 10,000×g supernatant was again centrifuged at 40,000×g and the apparent irGnRH in the supernatant and precipitate determined. Finally, the 40,000×g supernatant was subjected to ultracentrifugation at 100,000×g for 30 min. The C-ase-1 activity in the supernatant and precipitate was determined.

TABLE 2

| Differential Centrifugation of C-ase-1 PLACENTAL EXTRACT (100%) | | |
|---|---|---|
| Centrifugation 4000 × g, 4° C. | Supernatant 1 | Precipitate 1 (6.6%) |
| Centrifugation of Supernatant 1 10,000 × g, 4° C. | Supernatant 2 | Precipitate 2 (0.5%) |
| Centrifugation of Supernatant 2 40,000 × g, 4° C. | Supernatant 3 | Precipitate 3 (0.7%) |
| Centrifugation of Supernatant 3 100,000 × g, 4° C. | Supernatant 4 (90.8%) | Precipitate 4 (1.4%) |

(2) Ultrafiltration

Diaflo ultrafiltration (Amicon Corp., Danvers, Mass.) of placental extracts were performed using PM30, PM10, YM100, YM30, YM10 and YM02 membranes and the C-ase-1 activity of the retentate and the filtrate measured.

(3) Gel Permeation Chromatography

Sephadex gel chromatography (G-150, 90×5 cm equilibrated in Tris-DTT-pepstatin) was eluted with the column buffer (collecting 20 ml fractions) and activity in each fraction quantitated using the GnRH-RIA. Molecular weight was estimated by comparison to bovine serum albumin (BSA) and synthetic GnRH.

HPLC analyses of C-ase-1 activity was done, using a molecular sizing Bio-Rad TSK-250 column (Bio-Rad Laboratories, Richmond, Calif.) equilibrated and eluted with 0.01M Tris, 0.001M DTT, pH 7.2 (Tris-DTT) at a flow rate of 1.0 ml per minute. Absorbency was monitored at 280 nm. Molecular weight was estimated by comparison to standards (thyroglobulin, gamma globulin, albumin, ovalbumin, myoglobin, vitamin B-12). Rechromatography of the fractions containing C-ase-1 activity was done on the TSK-250 column to confirm its elution pattern.

(4) Dissociation and Denaturation Studies

C-ase-1 was incubated with two concentrations of trypsin (0.02 and 1 mg/ml) for 30 min at 37° C. The remaining activity was determined following HPLC chromatography (as described above). The C-ase-1 incubated with 1 mg/ml trypsin was further incubated at room temperature for 1 h and the remaining activity was again assessed following HPLC chromatography.

Attempts to dissociate or denature C-ase-1 activity were done using guanidine, urea, Triton X-100, acid, or boiling. Incubations of the placental extracts with either 3 or 6M guanidine, pH 7.5 for 0, 10, 20, 30, 40, 60, 120, or 240 min at room temperature were performed and the remaining C-ase-1 activity determined. Similar timed studies using 1 or 2M urea were also done. Also the effect of 1% Triton X-100 for 3 h at room temperature was studied.

(5) GnRH Binding Studies

Placental extracts (75 ml) were incubated with $I^{125}$-GnRH (5,000,00 cpm/ml final concentration) overnight at 4° C. Control incubations of both placental extracts and diluent (no labelled GnRH added) $I^{125}$-GnRH and buffer (no placental extract added) were also done. Sephadex chromatography (G-150, 90×5 cm in Tris-DTT-pepstatin) was performed on each incubate to determine possible displacement of the low molecular weight $I^{125}$-GnRH to the area of the high molecular weight protein, C-ase-1. Eluates were monitored for radioactive counts.

(6) GnRH Recovery: Chorionic Peptidase 1 Inactivation Studies

GnRH (30 ng in 100 microliter) was incubated with C-ase-1 (2.0 ng apparent irGnRH/100 microliter), 100 microliter of buffer (Tris-DTT) and 50 microliters of bromophenol blue (0.50 mg/ml) and dextran blue (15 mg/ml). Incubation was for 0 or 20 hours at 4° C. C-ase-1 activity was quantitated before and after chromatography of the incubates on Sephadex G-100 (1×20 cm, Tris-DTT buffer) in the eluted fractions (1 ml). Control incubations of C-ase-1 or GnRH alone were similarly studied. Additional incubations in the presence of alpha-1-anti-trypsin (10 mg/ml), 2-nitro-4-carboxyphenyl, N,N-diphenyl-carbamate (1.8 nm), pepstatin (0.01%), bacitracin (111-014, 300 U/ml), para-amino benzamidine (0.395-50 mM), EDTA (4 mM), diisopropylfluorophosphate (1 k mM), DMSO, amastatin (10 ug/ml [microgram], bestatin (10 ug/ml [microgram]), leupetin (20 ug/ml [microgram]), and aprotinin (0.13 TIU/ml) or after exposing C-ase-1 to pH 5.0 for 10 min. then readjusting to pH 7.2, or heating for 2 min. at 60° C., were studied. Similar studies were done with hCG, hCS, SRIF, CRF, TRH, antiotensin II and oxytocin (OXY) with and without bacitracin to determine the specificity of the C-ase-1 activity.

EXAMPLE 3

Isolation of Chorionic Peptidase 1 from Human Placenta

Extraction of an individual lyophilized, pulverized full term placenta was done at room temperature, beginning with two acetone washes (1000 ml each). This initial step defatted the tissue without extracting the apparent GnRH immunoreactivity, and was followed by extraction of the apparent GnRH immunoreactivity from the acetone precipitate with 300 ml of 0.01M Tris-DTT-pepstatin buffer. Pepstatin was also included in the buffer to preserve the apparent GnRH immunoreactivity during storage and purification, and DTT to prevent aggregation of the material with apparent GnRH immunoreactivity. The placental suspension was centrifuged in a IEC PR-6000 centrifuge at 4° C. at 3000×g for 30 min.

The initial placental extraction was performed as described above. Following removal of any precipitate by centrifugation, the supernatant was purified by chromatography on Sephadex G-150 (5×90 cm, in Tris-DTT-pepstatin) at 4° C. Approximately 80 ml of extract was applied to a column; thus, two columns were needed for each placenta. The elution of C-ase-1 activity was determined using the two different GnRH-RIAs. The fractions containing C-ase-1 (600 ml, Ke=0.27–0.40) were pooled and concentrated using Diaflo hollow fiber-H1P30-20.

This partially purified concentrate (60 ml) having C-ase-1 activity was mixed with 60 ml of Blue-Sepharose and the supernatant was applied to a DEAE-Sepharose column (2.5×30 cm), equilibrated in Tris-DTT. After application of the sample, the column was washed with the Tris-DTT (350 ml), followed by Tris-DTT containing a 0.10M NaCl (1000 ml). The C-ase-1 was then eluted while washing with Tris-DTT containing 0.11M NaCl (1600 ml). A final wash (400 ml) of Tris-DTT containing 1M NaCl was applied. The eluates containing C-ase-1 activity were pooled, concentrated to 40 ml using a Diaflo hollow fiber, H1P30-20, then incubated overnight at 4° C. with 0.5 ml of anti-HSA coupled to Staph A-Sepharose as described previously (Schneider, et al. (1982), *J. Biol. Chem.*, 257:10766). The Sepharose was then removed by filtration and the supernatant containing isolated C-ase-1 collected.

Figure 10:
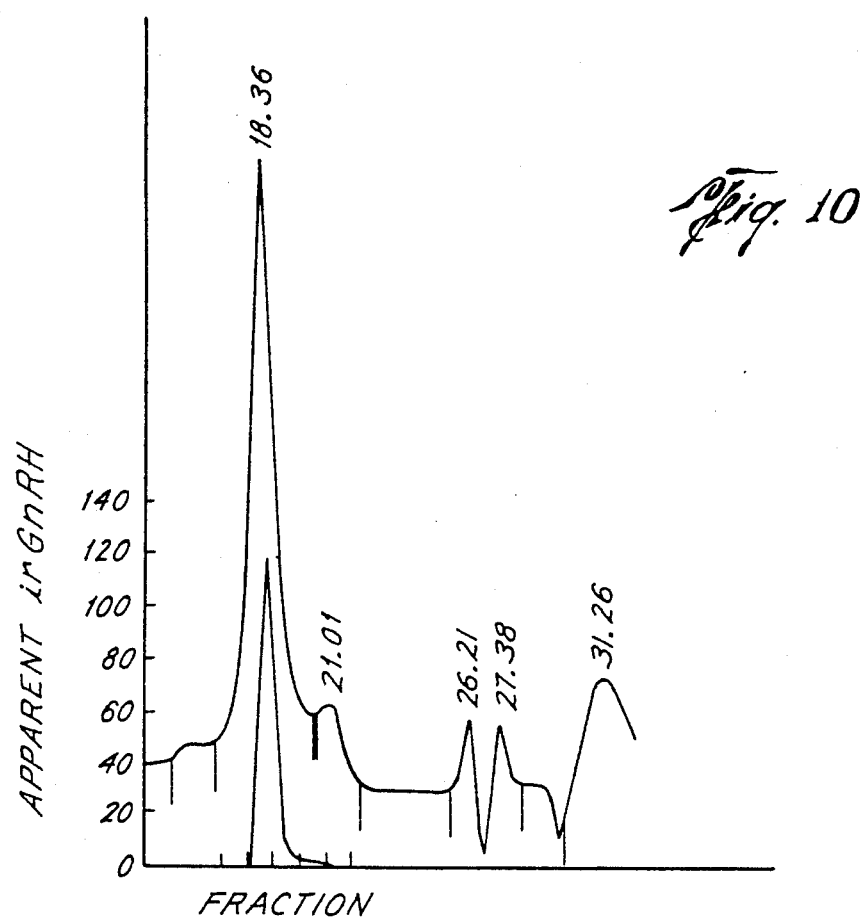
FIG. 10 shows the HPLC purification of C-ase-1 PAS-DROS-pool. 50 microliters of concentrated PAS- DROS was applied and fractions were collected from 18 to 22 minutes of 0.2 ml. each.

This fraction was then further purified by HPLC on a ultropac TMSK-column (7.5×30 cm, LKB) (FIG. 10). The mobile phase buffer was 100 mM $Na_2SO_4$, 20 mM $Na_2PO_4$, 1 mM DTT, pH 7.2 washed at 1 ml/min. The fractions with C-ase-1 activity were pooled. The specific activity of this highly purified, final fraction was 1.2 ug apparent irGnRH/mg protein, therefore achieving an approximate 30,000×purification from a crude placental extract.

EXAMPLE 4

Physical and Chemical Characterization and Assembly of Purity of C-ase-1

The isolated C-ase-1 obtained following DEAE-Sepharose chromatography was studied by polyacrylamide gel electrophoretic analysis (PAGE). PAGE was performed after pre-incubation of the purified material for 20 min with 1% SDS at 90° C. The sample was mixed 1:1 with 30% glycerol and applied to polyacrylamide slab gels of 10% in a Borate-Tris buffer, pH 7.6, containing 0.1% SDS and 0.001M DTT, and electrophoresis was performed at room temperature with the same buffer. Coomassie Brilliant Blue R-250 (0.1% in $CH_3OH:H_2O:HOAc$ [5:5:1]) for 1 h was used to stain the protein. The gels were destained by washing with $CH_3COOH:CH_3OH:H_2O$ (10:5:85) 10 times. A single band was observed and its corresponding molecular weight estimated by comparison to standard proteins (phosphorylase B, BSA, ovalbumin, carbonic anhydrase, trypsin inhibitor and lysozyme) run concurrently on the same gel in separate lanes.

EXAMPLE 5

Determination of C-ase-1 Biological Activity (1) Activity on Pituitary LH and FSH Release in Vivo.

Figure 11:
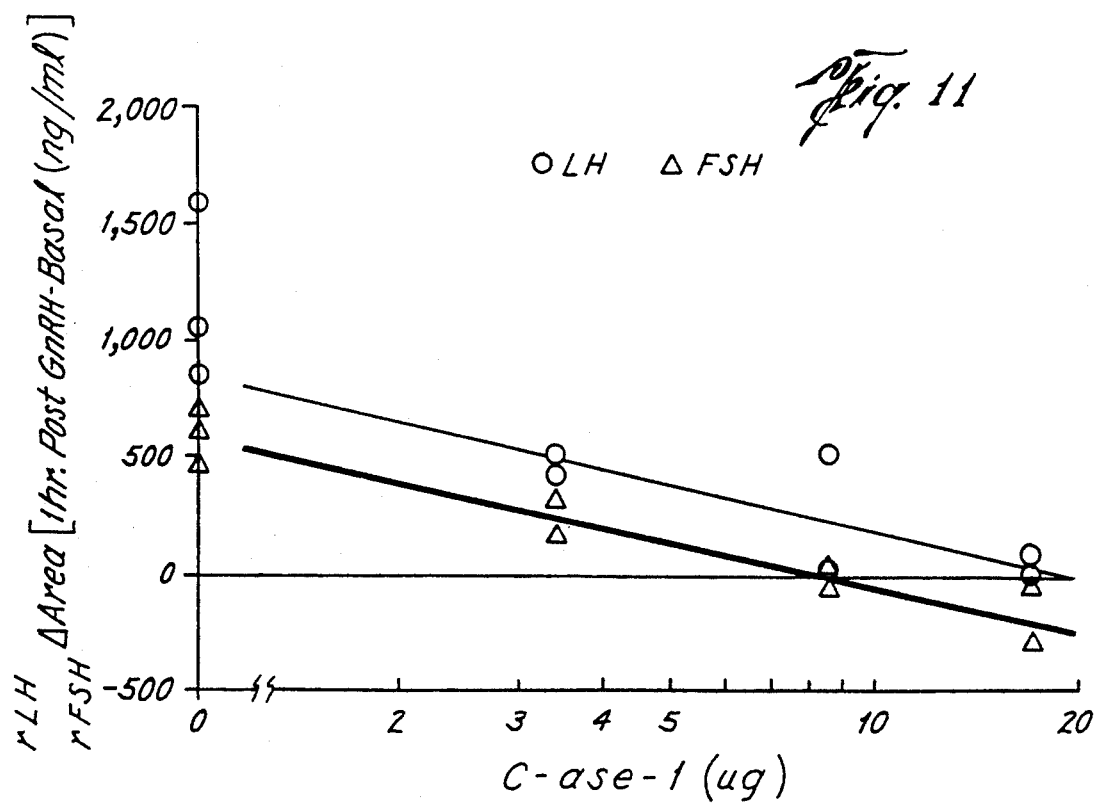
FIG. 11 shows the dose-releated inhibition of GnRH stimulated LH and FSH release by C-ase-1 in castrated rats.
Figure 12A:
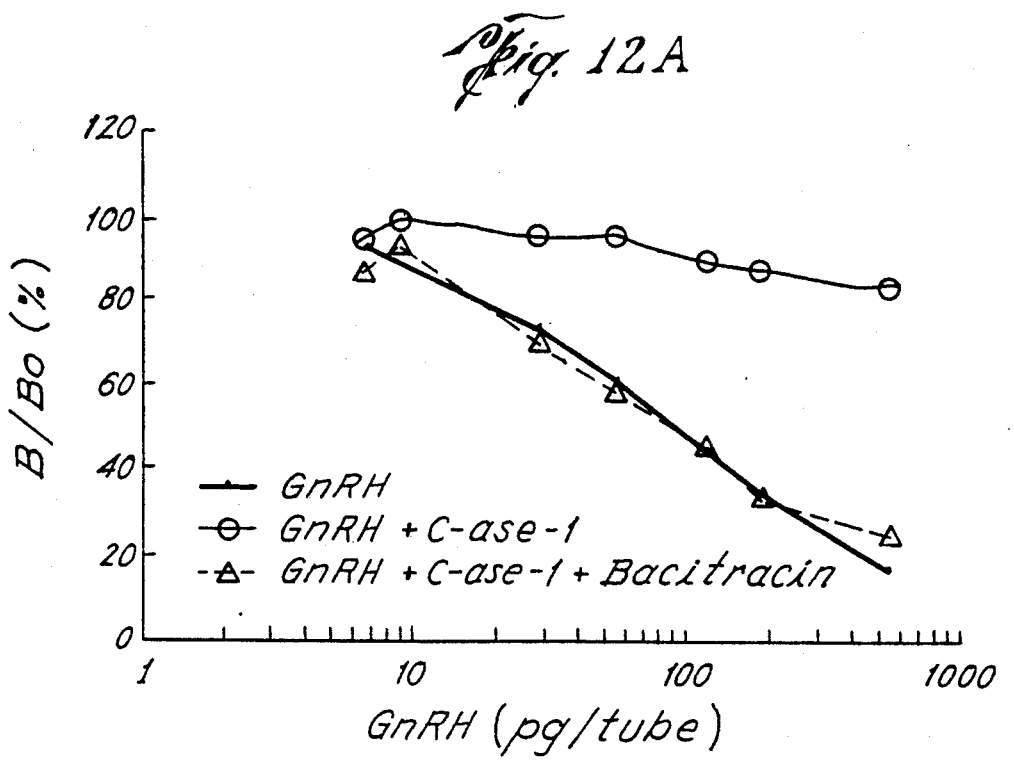
FIG. 12 shows the recovery of GnRH after incubation with C-ase-1 with or without bacitracin.
Figure 12B:
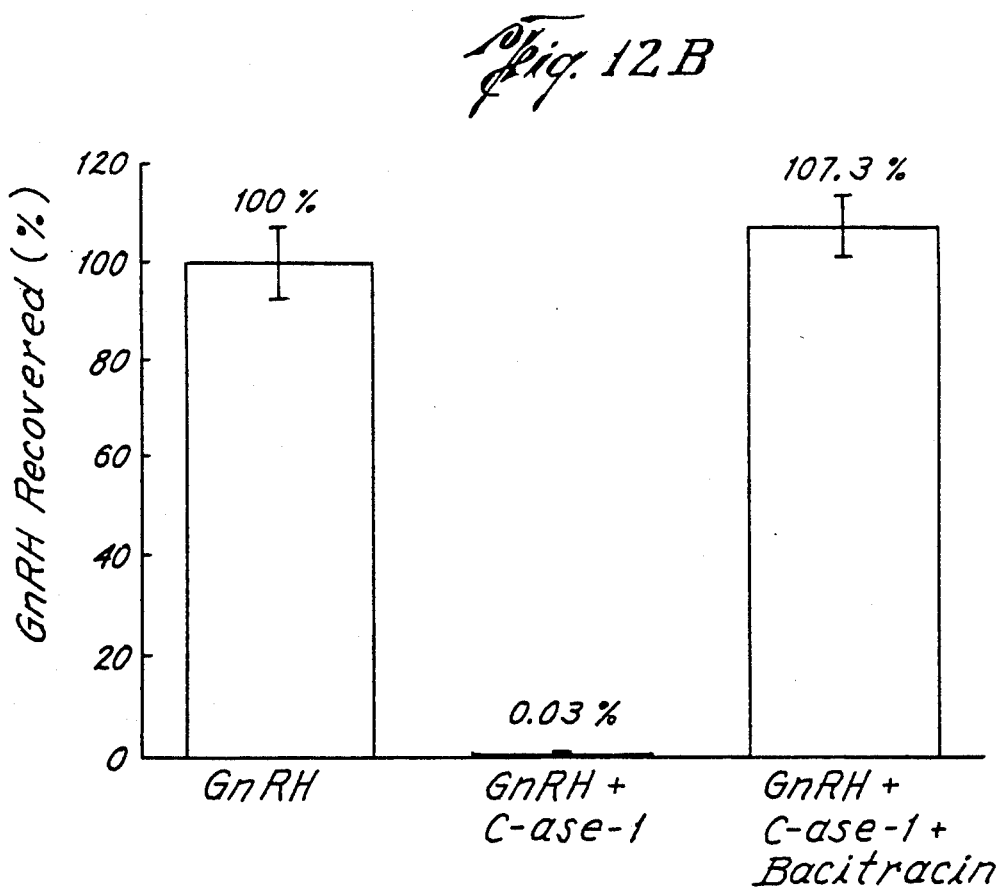

The effect of C-ase-1 on the GnRH-stimulated release of FIG. 11) Castrated adult male rats were catheterized under ether anesthesia, the right external jugular vein was exposed and a polyethylene cannula (od 0.038 in) inserted down to the level of the right atrium. The rats were allowed to recover for at least 3 h before the studies were begun. Thus, these studies were performed in unanesthetized animals. Two basal blood samples were drawn 10 min apart, then C-ase-1 (8.5, 13.6, 17.0 micrograms C-ase-1) together with 500 ng GnRH (n=7) was injected as a single bolus. Controls (n=4) were injected with only GnRH. Blood was drawn at 0, 10, 20, 30, 40, 50, 60, 75, 90 and 120 min. Plasma (EDTA) was collected and stored frozen at −20° C. until assayed for LH and FSH.

EXAMPLE 6

Radioimmunoassays

Radioimmunoassays were done as described by Siler-Khodr et al., (1986) (*Biol. Reprod.*, 34:245) with the exception that separation of bound hormone for GnRH was by ethanol precipitation and for other assays by incubation with magnetizable polymer beads coated with anti-rabbit globulin (Amersham, Arlington Heights, Ill.) which was then precipitated using a magnetic base.

(1) GnRH-RIAS

Two different antisera were used to detect and quantitate the C-ase-1 activity of the human placenta. The degradation of GnRH, by C-ase-1, inhibited the binding of $^{125}I$-GnRH to either of these antisera; thus an apparent GnRH immunoreactivity was effected. Therefore the results are reported as apparent irGnRH.

Synthetic GnRH was radio-iodinated by the method of Hunter et al.(1962) (*Nature*, 194:495) and desalted on a CM-cellulose column as described previously (Khodr & Siler-Khodr, 1980). $^{125}I$-GnRH (20 pg/100 microliters) was added to each assay tube. One of the GnRH antibodies used (UZ-2; Miles Laboratory, Elkhart, Ind.) was made to a GnRH-bovine serum albumin (BSA) conjugate and used at a final dilution of 1/30,000. There was a 20% cross-reaction with the C-terminal nonapeptide. Other fragments and the free acid had <2.5% cross-reactivity. No significant cross-reactivity (<0.001) with IGF-1, OXY, hCG, beta-hCG, alpha-hCG, hCS, CRF, SRIF, IGF-1 or angiotensin-II was observed. The assay sensitivity was 8 pg/tube and the within and between assay coefficients of variation were 3% and 7%, respectively, at 70% of the maximum binding.

The other GnRH antibody used was a monoclonal antibody to GnRH derived from clone $P_8 16_{13}$ in the laboratory of Dr. Talwar, New Delhi, India. This antiserum was used at a final titre of 1/1,000,000 and was highly specific for GnRH. Standard was synthetic GnRH. The antiserum was directed to the N-terminal pentapeptide sequence of GnRH, and the C-terminal amide. No significant cross-reactivity (<0.001) with other placenta peptides was found. Assay sensitivity was 4 pg/tube and the within and between coefficients of variation were 5% and 9%, respectively, at 70% of the maximum binding.

(2) hCG

Measurement of hCG was done as described previously (Siler-Khodr, et al. (1986), *Biol. Reprod.*, 34:245) using a highly specific antiserum to the beta subunit of hCG (#H971675; Dr. V. Stevens) and intact hCG (#CR119) as standard. Assay sensitivity was 0.100 ng/tube, and within assay coefficients of variation was 10.0% at 70% of the maximum binding.

(3) hCS hCS was measured as previously described (Siler-Khodr et al. (1986), *Biol. Reprod.*, 34:245) using a highly specific antiserum to hCS (#CT3399) and purified hCS as standard. Assay sensitivity was 0.19 ng/tube and intra-assay coefficient of variation was 6.6% at 70% of the maximum binding.

(4) CRF

CRF was determined using a specific antiserum at a final dilution of 1/150,000. Synthetic Tyr-CRF (Sigma, St. Louis, Mo.) was iodinated by the method of Hunter et al., (1962) (*Nature,* 194:495) to a specific activity of 275 microCi/microgram and desalted on a Sephadex G-50. Label (10 pg) was added to every tube. The standard was synthetic human CRF (Sigma, St. Louis, Mo.). Incubation was overnight at 4° C. Assay sensitivity was 100 pg/tube. The mean intra-assay coefficient of variation was 3% at 70% of the maximum binding.

(5) SRIF

SRIF was measured using a specific antiserum (purchased from Chemicon Int., Los Angeles, Calif.) at a final dilution of 1/10,000 of their ampoule. Tyr-SRIF (Sigma, St. Louis, Mo.) was iodinated by the method of Hunter et al., (1962) (*Nature,* 194:495) to a specific activity of 250 microCi/microgram, was desalted on Sephadex G-25 and 20 pg added to each assay tube. Incubation was at 4° C. overnight. Assay sensitivity was 30 pg/tube. No significant ($<0.001$) cross-reactivity with GnRH, TRH, alpha or beta-MSH, beta-endorphin or arginine vasopressin was found.

(6) Oxytocin

Oxytocin, (OXY), was measured using a specific antiserum (Chemicon Int., Los Angles, Calif.) at 1/40,000 of the supplied ampoule. Standard was obtained from Sigma (St. Louis, Mo.). OXY was iodinated by the method of Hunter et al., (1962) (*Nature,* 194:495), in a specific activity of 300 microCi/microgram, desalted on Sephadex G-15 and 20 pg/tube added to each assay tube. Incubation was for 20 hours at 4° C. Assay sensitivity was 4 pg/tube. Cross-reactivity with SRIF and vasopressin was $<2\%$.

(7) Angiotensin II

Angiotensin II was measured using a specific antiserum (Schwartz-Mann, Cleveland, Ohio) at a final dilution of 1/40,000 of the supplied ampoule. Standard was angiotensin II (Sigma, St. Louis, Mo.). Angiotensin II was iodinated to a specific activity of 250 microCi/microgram by the method of Hunter et al., (1962) (*Nature,* 194:495), and desalted using Sephadex G-10. Incubation was for 20 hours at 4° C. Assay sensitivity was 2 pg/tube.

(8) TRH

TRH was measured using a specific antiserum (purchased from Chemicon Int., Los Angeles, Calif.) at a final dilution of 1/4,500 of provided ampoule. Standard was TRH (Sigma, St. Louis, Mo.). Radioiodinated TRH, having a specific activity of 325 microCi/microgram, was produced by the method of Hunter et al., (1962) (*Nature,* 194:495), desalted with Sephadex G-10, and 20 pg added to each assay tube. Incubation was for 20 hours at 4° C. Assay sensitivity was 3 pg/tube. No significant cross-reactivity ($<0.001$) with the free acid of TRH, its fragments or GnRH was found.

(9) Rat LH

Measurement of rat LH was done using an antiserum to ovine LH (#15) at a final dilution of 1/75,000. Purified ovine LH (#LER 1374A provided by NIAMDD) was radioiodinated using the method of Hunter et al., (1962) (*Nature,* 194:495), to a specific activity of 300–400 Ci/microgram and 0.100 ng was added to each tube. Standard was rLH (RP-1, provided by the NPA). The standard or sample and antiserum were preincubated overnight at 4° C. Label was then added and the incubation continued for another day at 4° C. before adding the second antibody. C-ase-1 did not affect the binding in this assay.

(10) Rat FSH

A specific antiserum (provided by to the NIAMDD) was used at a final dilution of 1/5,000 in assay purified hFSH (NIH, 1-3) was radioiodinated according to the method of Hunter et al., (1962) (*Nature,* 194:495), to a specific activity of 300–400 microCi/microgram and 0.100 ng was added to each tube. Standard was rFSH (RP-1, provided by the NIAMDD). The standard or sample and antiserum were preincubated for 2 days at 4° C. Then label was added and the incubation continued for 3 days at 4° C. before adding the anti-rabbit gamma globulin. Assay sensitivity was 15 ng/tube and the coefficient of variation within and between assays was 1.4% and 5.2%, respectively, of the maximum binding. C-ase-1 activity did not affect the binding in this assay.

EXAMPLE 7

Protein Measurement and Statistical Analysis

Protein concentration was determined by the Lowry method as described by Bradford (1976) (*Anal. Biochem.,* 72:248), Biuret method or by absorbance at 280 nm using crystalline human serum albumin as standard. For release of each hormone from a given placenta the variation of the response with C-ase-1 was compared to that of controls or that of GnRH-stimulated culture using two-way analysis of variance. Dose-response analysis was done using linear regression analysis.

EXAMPLE 8

Characterization of C-ase-1 Activity

C-ase-1 activity in the placental extract, did not precipitate during differential centrifugation at 4,000 to $100,000 \times g$ (Table 2), i.e., 4,000, 10,000, 40,000 and $100,000 \times g$ precipitates had only 6.6%, 0.5%, 0.7% and 1.4% of the C-ase-1 activity, respectively.

Diaflo filtration resulted in retention of 99% of the C-ase-1 activity using membranes as large as a PM-30, which indicates an apparent mol wt of $>30,000$ daltons. However, the C-ase-1 was not retained using a YM100 membrane, thus its molecular weight was $<100,000$ daltons. Chromatography of the placental extracts on Sephadex G-150 demonstrated that this C-ase-1 activity had an apparent mol wt of 50,000–70,000, since it eluted as a single peak with a Ke=0.27–0.40 (FIG. 9).

Using an HPLC permeation column (Bio-Rad TSK-250), chorionic peptidase activity eluted as a single protein peak having a molecular weight of approximately 58,000 daltons (FIG. 10). Reapplication of the eluate containing C-ase-1 activity to the HPLC system resulted in the same elution pattern as before.

EXAMPLE 9

Denaturation Studies

Trypsin digestion using 0.02 mg trypsin/ml for 30 min at 37° C. had no effect on the C-ase-1 activity. However, incubation with 1 mg trypsin/ml for a similar time resulted in a 60% loss of C-ase-1 activity. Further incubation of C-ase-1 in the 1 mg/ml trypsin solution for 1 h at 21° C. resulted in a further loss of activity to 10% of its initial value. HPLC analyses of the incubates with any remaining activity revealed that the remaining C-ase-1 activity still eluted as molecule of approximately 58,000 daltons.

Attempts to dissociate the C-ase-1 activity to a smaller molecular size with guanidine (3M or 6M) or urea (1M or 2M) after 4 h of incubation at room temperature were unsuccessful. These treatments denatured and totally destroyed the C-ase-1 activity. This loss of activity was immediate for guanidine and time-dependent for urea (Table 3).

TABLE 3

Effects of Urea and Guanidine (pH 7.5) on C-ase-1 Activity in Human Placental Extracts

| Time (min) | % of Original Apparent irGnRH | | | |
|---|---|---|---|---|
| | Guanidine $H_2O$ | Urea (3M) | Urea (2M) | Urea (1M) |
| 0 | 100 | <6.5 | 72.7 | 100.0 |
| 10 | — | — | 59.4 | 91.0 |
| 20 | — | — | 29.2 | 91.0 |
| 30 | — | — | 12.4 | 79.2 |
| 60 | 100 | — | 4.8 | 51.1 |
| 90 | — | — | 4.6 | 35.3 |
| 120 | — | <6.5 | 2.5 | 30.8 |
| 240 | 100 | <6.5 | 1.6 | 30.9 |

When synthetic GnRH was incubated for 4 with guanidine or urea, there was no loss of immunoactivity. Exposure to Triton X-100 for 3 h did not destroy the C-ase-1 activity, nor did it alter its chromatographic mobility, i.e. it still eluted as the high-molecular weight protein. Complete inactivation of the C-ase-1 activity was effected by heating at 60° C. for 2 min or pH 5.0 for 10 min.

When placental extracts containing C-ase-1 activity and $^{125}$I-GnRH were incubated at 4° C. overnight and then subject to Sephadex G-150 column chromatography, <0.001% of the radioactivity eluted in the high-molecular size area with 99% in the GnRH-salt area. This was similar to the elution of the control column, i.e. $^{125}$I-GnRH incubated with diluent only. Thus, the apparent irGnRH of C-ase-1 was not due to GnRH binding to a large molecule.

EXAMPLE 10

Peptide Inhibitor Studies

Figure 13A:
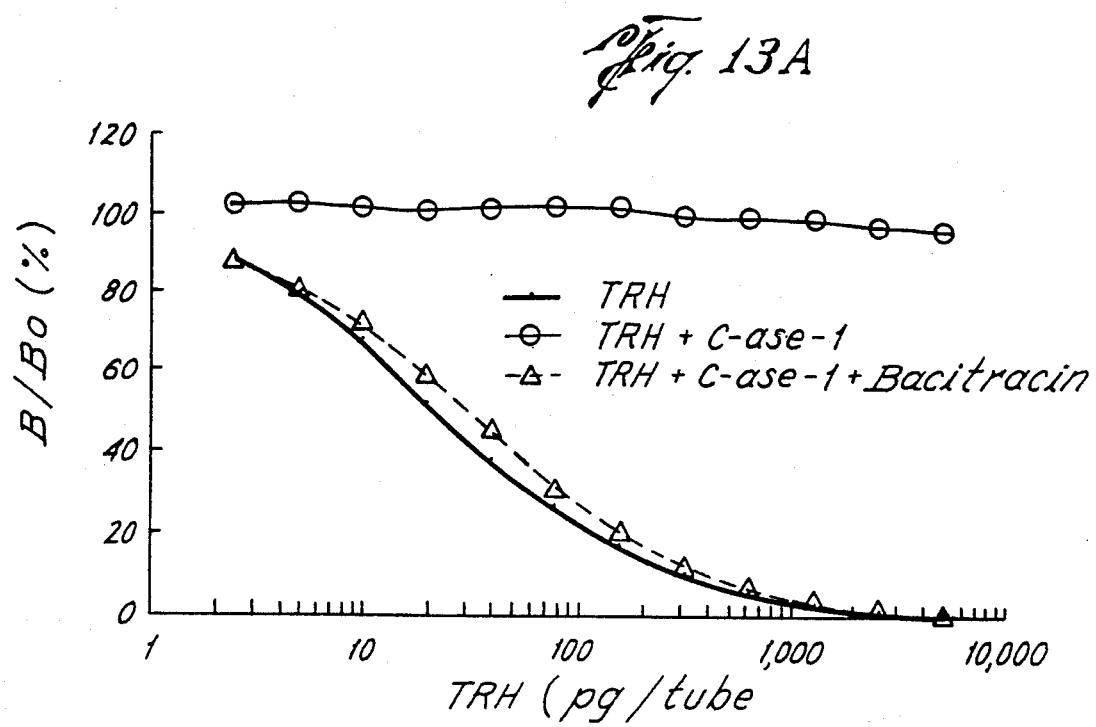
FIG. 13 shows the recovery of TRH after incubation with C-ase-1 with or without bacitracin.
Figure 13B:
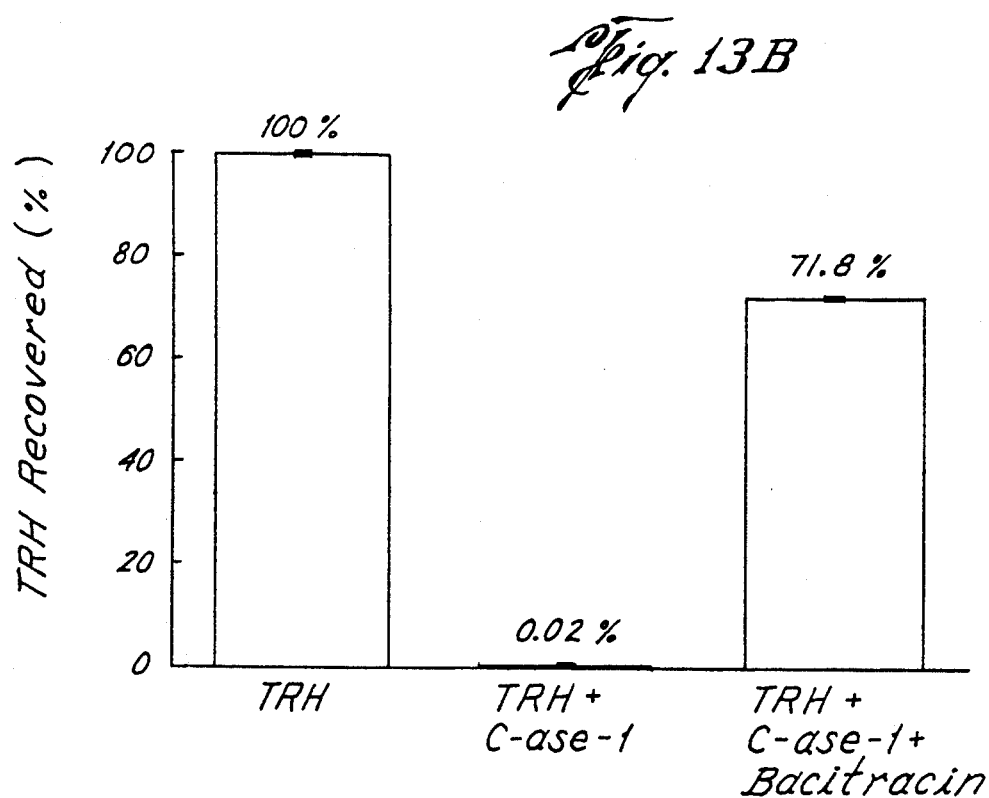

When exogenous GnRH was incubated with the chorionic peptidase for 24 h at 4° C., an undetectable level of GnRH was found. Sephadex G-100 chromatography of the incubates demonstrated a loss of GnRH compared to that recovered in the incubate without added C-ase-1 activity (FIGS. 9A and B). Total inhibition of the C-ase-1 ability to inactivate GnRH was effected with ≧200 U bacitracin (FIG. 13), 2.5 mM PAB, 1 mM diisopropylfluorophosphate, 2% DMSO (2%) (Table 1), or by exposing C-ase-1 to pH <5.0 for 10 min, or by heating it for 1.5 min at 60° C. The inhibition of C-ase-1 activity by bacitracin, and para-amino benzamidine were dose-related (Table 4).

TABLE 4

Dose Related Inhibition of C-ase-1 Inactivation of GnRH by Different Peptidase Inhibitors

| Bacitracin | | P-Amino-benzamidine | |
|---|---|---|---|
| Dose (U/ml) | GnRH* (ng/ml) | Dose (mM) | GnRH* (ng/ml) |
| With C-ase-1 | | | |
| 0 | 3 | 0 | 3 |
| 111 | 48 | 0.395 | 8 |
| 222 | 68 | 0.780 | 12 |
| 445 | 90 | 1.56 | — |
| 890 | 97 | 3.12 | 29 |
| 1790 | 96 | 6.25 | 29 |
| 3570 | 80 | 12.5 | 43 |
| 7140 | — | 25.0 | 89 |
| 14300 | 81 | 50.0 | 90 |
| No C-ase-1 | | | |

TABLE 4-continued

Dose Related Inhibition of C-ase-1 Inactivation of GnRH by Different Peptidase Inhibitors

| Bacitracin | | P-Amino-benzamidine | |
|---|---|---|---|
| Dose (U/ml) | GnRH* (ng/ml) | Dose (mM) | GnRH* (ng/ml) |
| 14300 | 84 | 50.0 | 85 |

*GnRH (100 microliter 100 ng/ml) was incubated with C-ase-1 (100 microliter, 20 ng apparent irGnRHase/ml), 50 microliters of molecular size markers and 100 microliters of various concentrations of inhibitor for 20 h at 4° C.

Figure 14A:
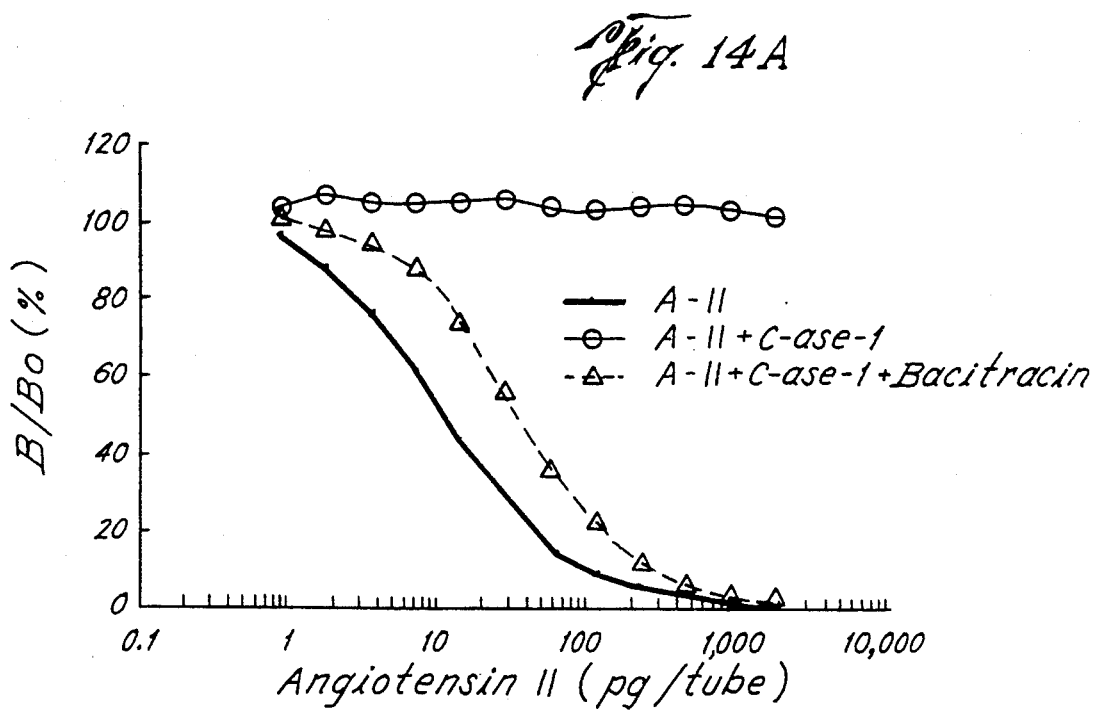
FIG. 14 shows the recovery of angiotensin II after incubation with C-ase-1 with or without bacitracin.
Figure 14B:
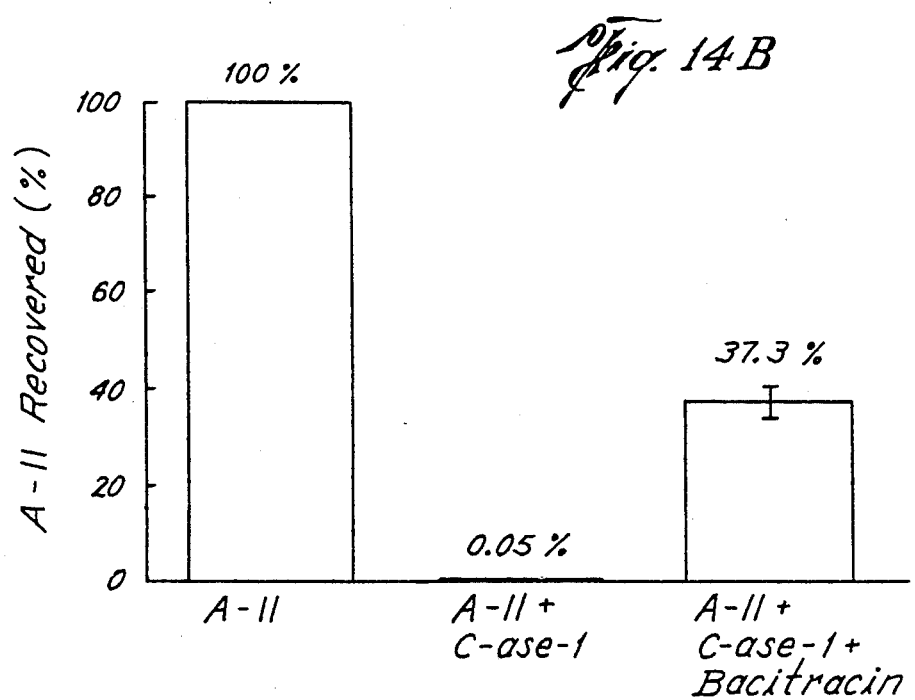
Figure 15A:
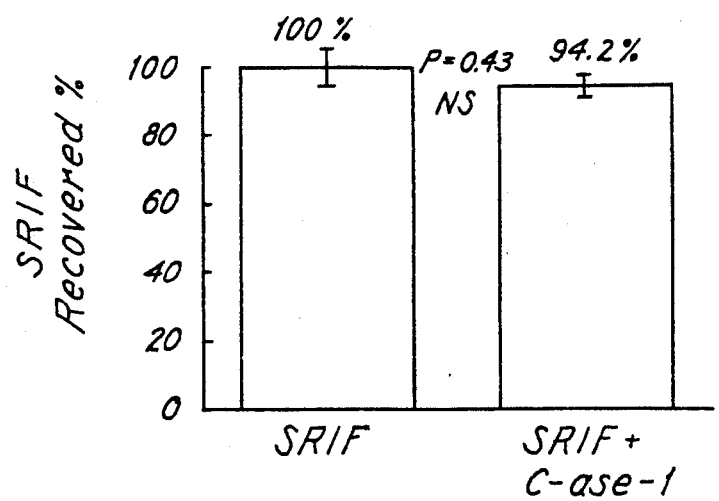
FIG. 15 shows the recovery of SRIF, CRF and hCG after incubation with C-ase-1.
Figure 15B:
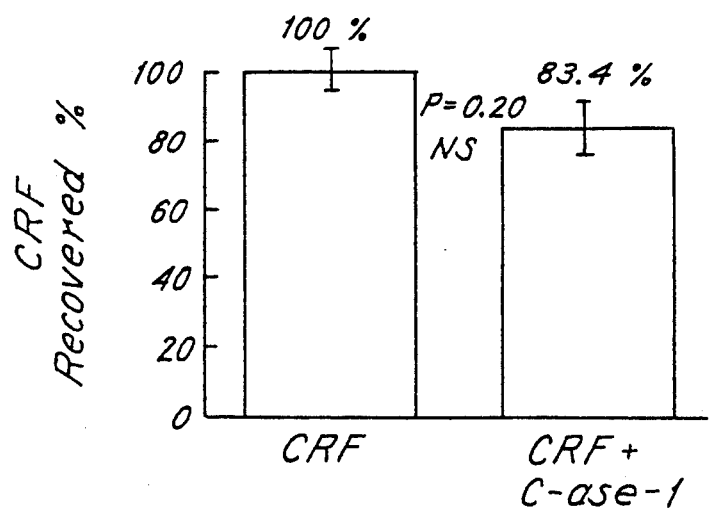
Figure 15C:
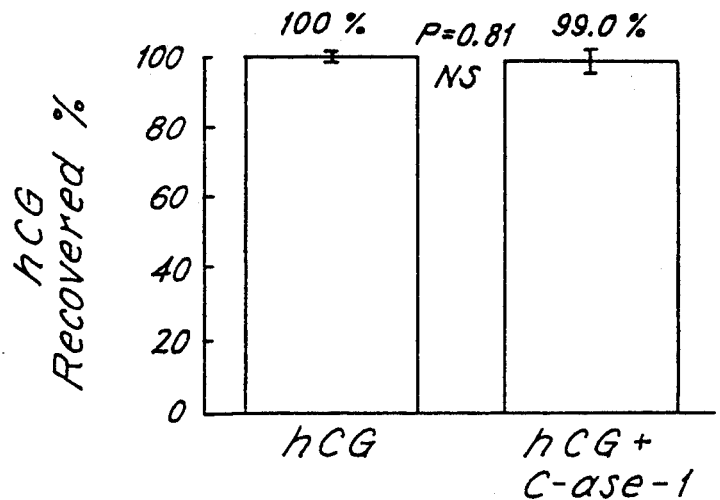
Figure 16A:
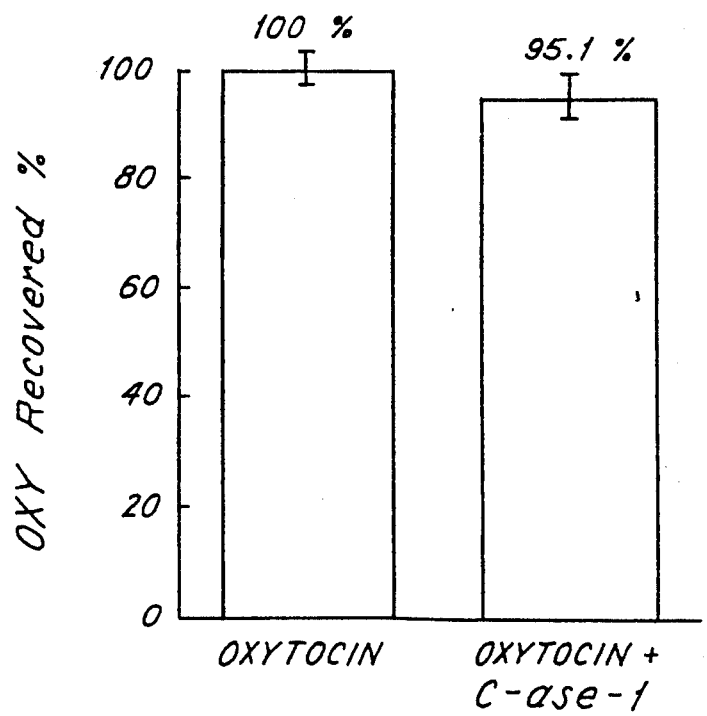
FIG. 16 shows the recovery of oxytocin after incubation with C-ase-1 in the presence of high or low concentrations of dithiothreitol.
Figure 16B:
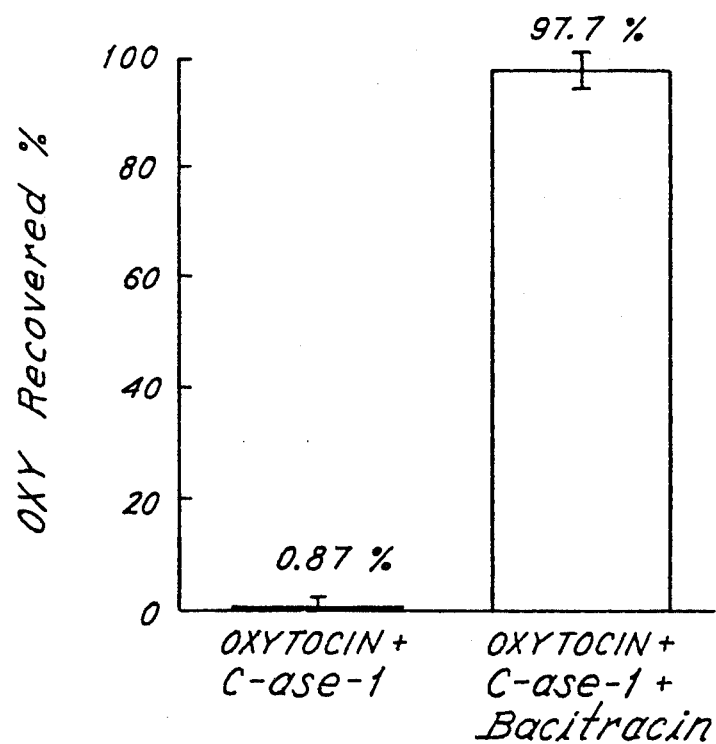

Alpha-1-anti-trypsin, 2-nitro-4-carboxyphenyl, N,N,-diphenyl-carbamate, pepstatin, amastatin, bestatin, leupetin, aprotinin or EDTA had no inhibitory effect on C-ase-1; e.g., no GnRH was recovered in these incubates. This C-ase-1 also inactivated the immunoreactive TRH (FIG. 13) and angiotensin II (FIG. 14), i.e., only <1% after either treatment was recovered. However, C-ase-1 was without effect on hCG, hCS, CRF. SRIF (FIG. 15), and OXY (FIG. 16), i.e., no loss of hCG, hCS, CRF, SRIF or OXY was observed after a 24 h incubation with C-ase-1. However, in the presence of 0.33 mM DTT, both OXY (FIG. 16) and SRIF were susceptible to inactivation by this C-ase-1, i.e., only <7% was recovered in the presence of DTT. Thus, the activity of C-ase-1 appeared specific for GnRH, TRH and angiotensin II.

Figure 17A:
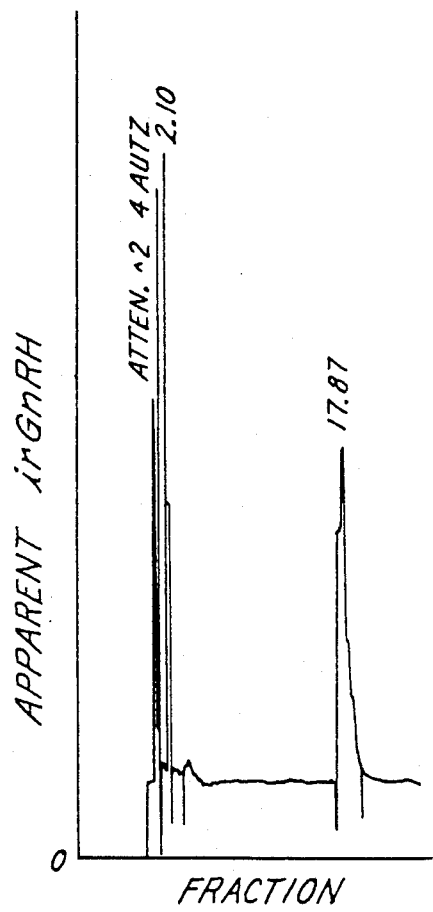
FIG. 17 shows the HPLC elution of (a) GnRH (17.87 min) and (b) fragments of GnRH produced by C-ase-1 (5.93 min.=Gly-$NH_2$; 25.08 min=dis $Gly^{1-}$0—$NH_2$GnRH).
Figure 17B:
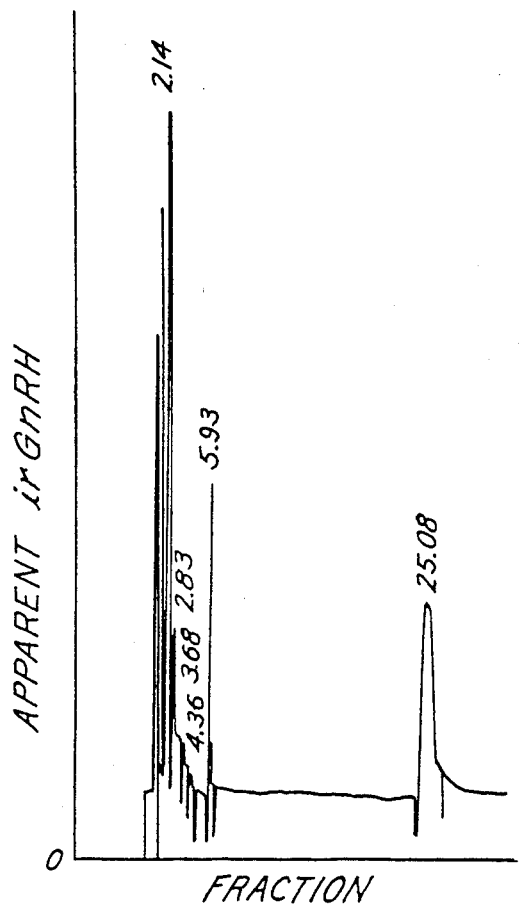

Following incubation of GnRH and C-ase-1, the resulting GnRH fragments produced were defined used HPLC (See FIG. 17). The incubation mixture was applied to a C-18 column (15×7.5 cm Rainin) and eluted with 19.5% acetonitrile in 100 mM $NaH_2PO_4$, pH 2.5. Two fragments were found. One in the area of Gly-$NH_2$ and another in the area of dis $Gly^{10}$-$NH_2$-GnRH. These GnRH products demonstrate that C-ase-1 acts as a post-proline peptidase on GnRH (See Table 5).

TABLE 5

GnRH
PGlu—His—Trp—Ser—Tyr—Gly—Leu—Arg—<u>Pro</u>—Gly—$NH_2$

Angiotensin II
Asp—Arg—Val—Tyr—Ile—His—<u>Pro</u>—Phe

TRH
PGlu—His—<u>Pro</u>—$NH_2$

Oxytocin
```
          DTT
           |
    ┌─────────────┐
Cys—Tyr—Ile—Gln—Asn—Cys—Pro—Leu—Gly—NH2
```

EXAMPLE 11

Isolation of C-ase-1 Peptidase from Human Placental Tissue

Fresh term placenta homogenized in Tris-DTT-pepstatin (this weight was derived by comparison of activity to the specific activity of the highly purified final fraction). In this extraction procedure, fresh term placenta were lyophilized and pulverized, then defatted by acetone extraction (Table 6, Step 1). The chorionic peptidase was then extracted from the precipitate with Tris-DTT-pepstatin buffer (300 ml)(Table 6, Step 2). Following centrifugation, approximately 18 micrograms of C-ase-1 activity was obtained in the 160 ml supernatant. Chromatography of equal volumes of the supernatant on two similar Sephadex G-150 columns (5 cm×90 cm equilibrated in Tris-DTT-pepstatin buffer) resulted in greater that 100% of the original C-ase-1 activity being eluted as a single peak with a Ke of 0.27-0.40 (FIG. 1). The increased activity may be due to removal of some inhibiting factor(s) (e.g., albumin).

Figure 2:
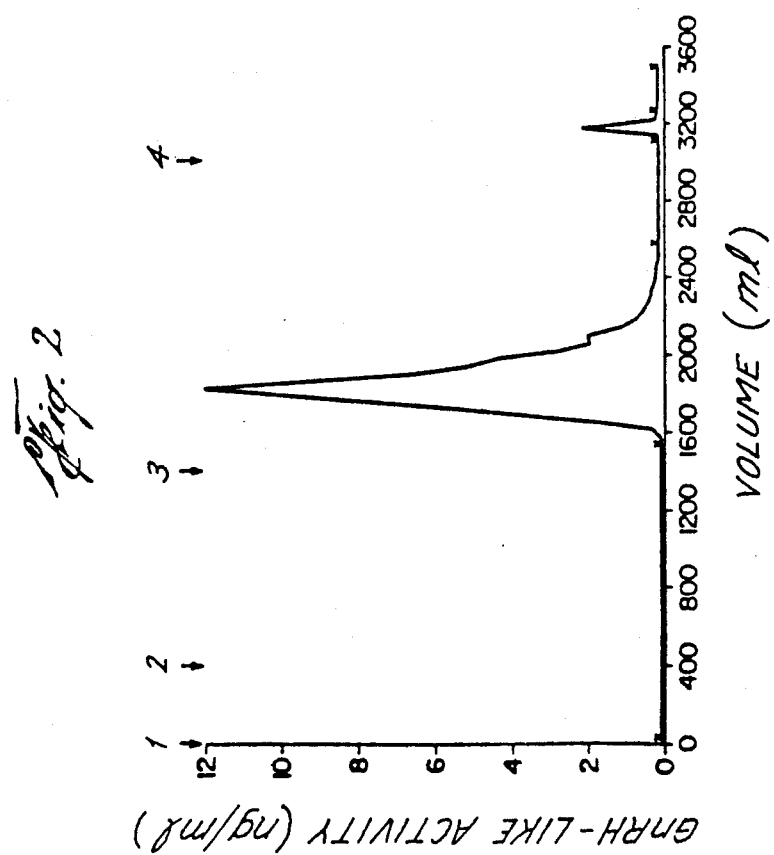
FIG. 2 describes the elution of chorionic C-ase-1 from DEAE-Sepharose (2.6×30 cm, 0.01M Tris, 0.001M DTT, pH 7.4). The column was first washed with column buffer 400 ml (1), and then column buffer with 0.10M NaCl (2). Chorionic C-ase-1 was eluted with 0.11M NaCl (3). Additional salt 1M NaCl (4) eluted another 2% of the C-ase-1 activity.
Figure 5:
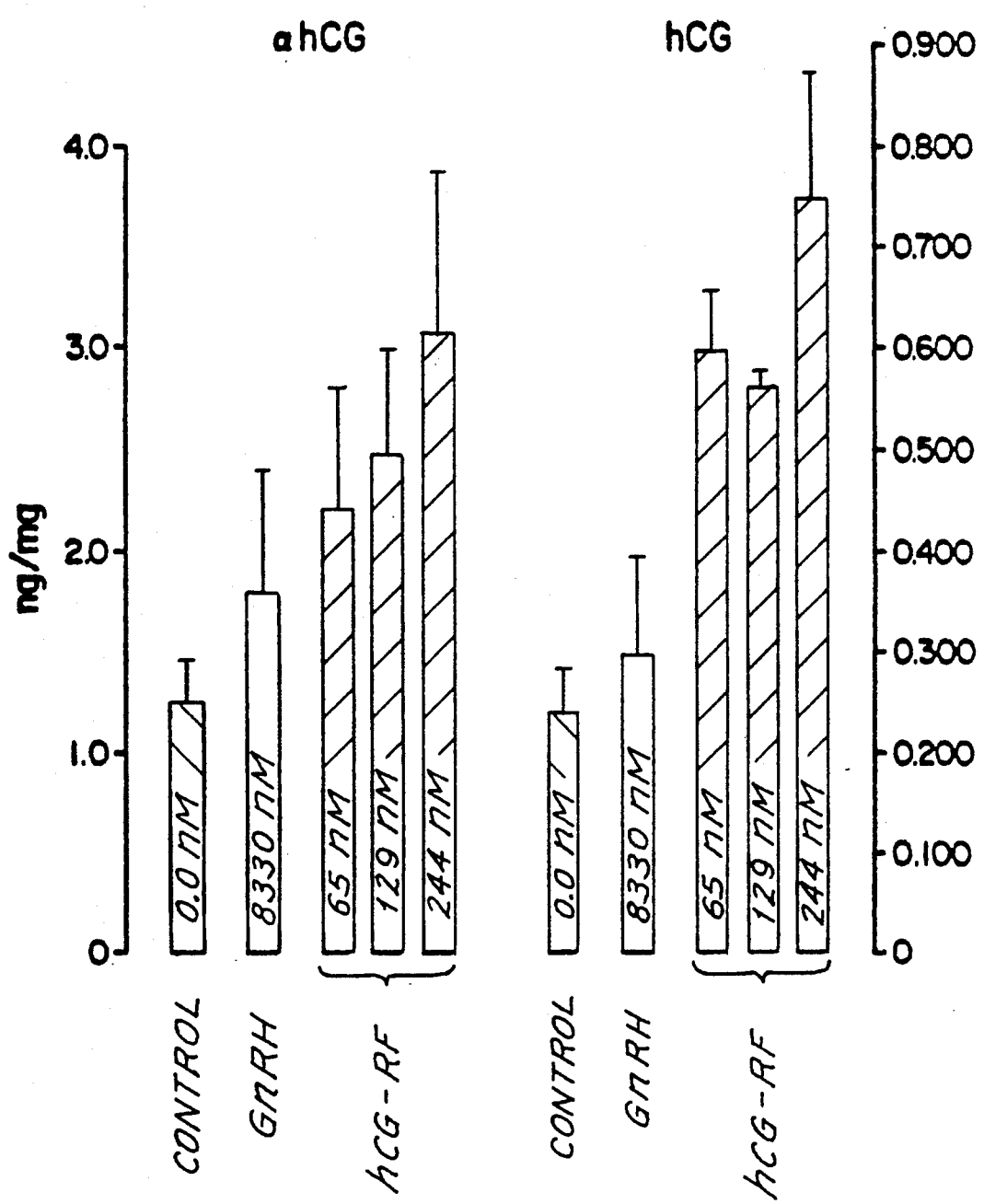
FIG. 5 describes the stimulation of alpha-hCG and hCG production (ng/mg placental tissue, mean ±SEM) on day 7 of term placental cultures incubated with GnRH or hCG-RF as compared to controls.
Figure 7:
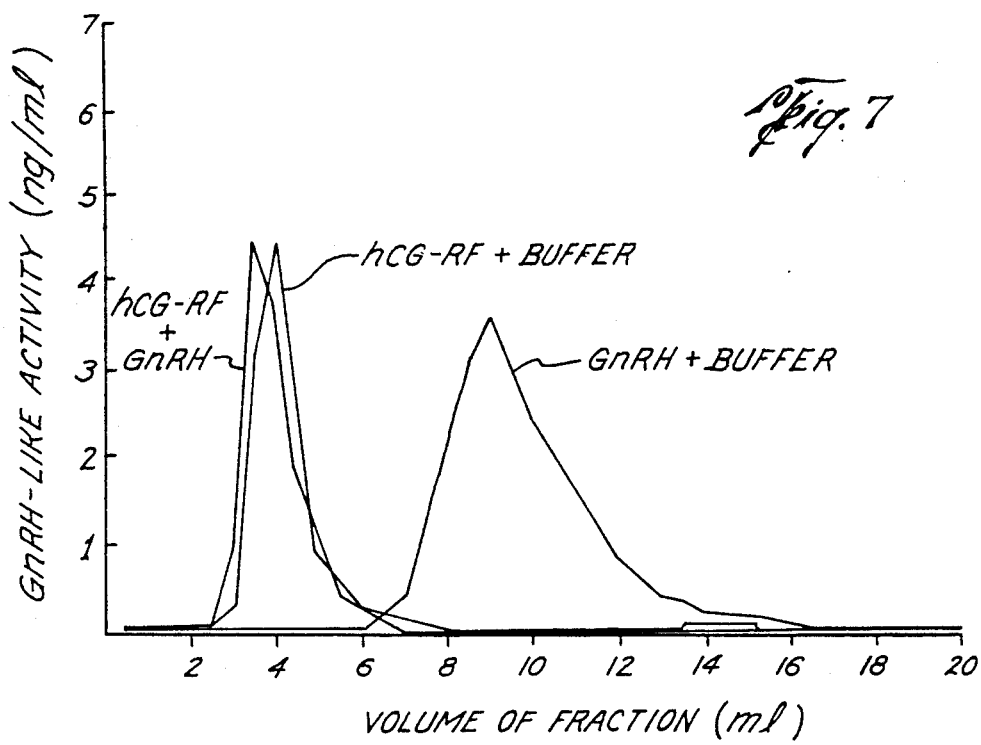
FIG. 7 shows the elution patterns for Sephadex G-150 of immunoactive GnRH treated with hCG-RF or with buffer.
Figure 8:
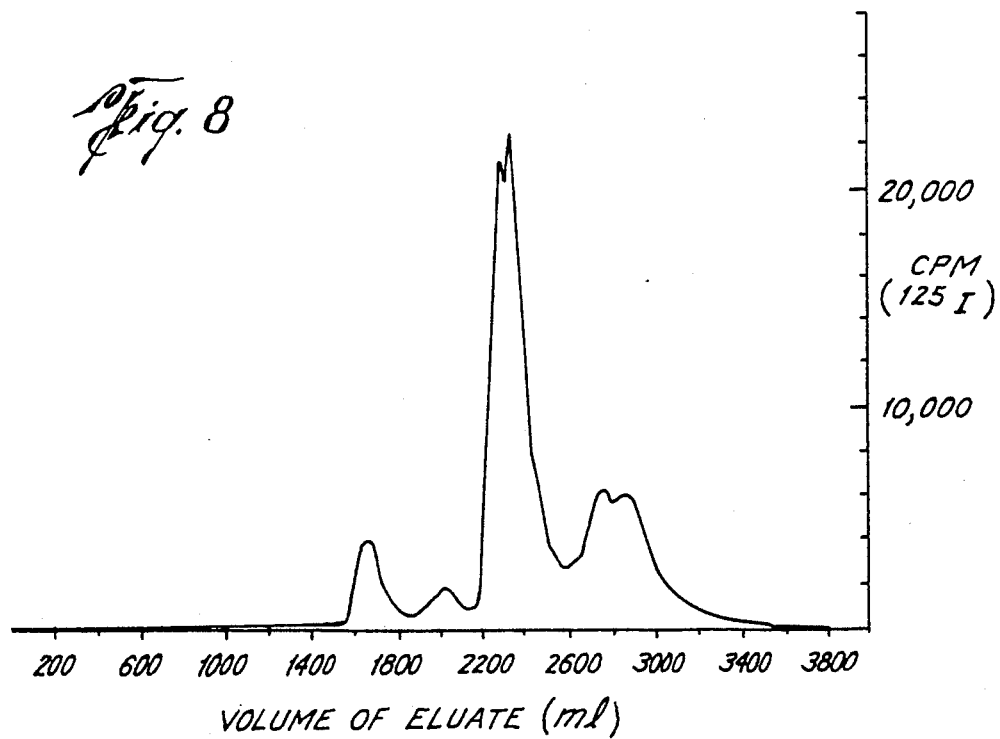
FIG. 8 shows a radioisotopic elution pattern from Sephadex G-25 of $^{125}$I-GnRH treated with an hCG-RF preparation.

The fractions with C-ase-1 activity were pooled (300 ml per column, total 600 ml) and concentrated by Diaflo HF-30 filtration (Table 6, Step 3). The retentate (60 ml) contained 99% of the activity originally extracted. Approximately 50-70% of the protein in this concentrate, was then removed by mixing with Blue Sepharose without a reduction in the C-ase-1 activity (Table 6, Step 3). This post-Blue Sepharose eluate was then applied to a DEAE-Sepharose column (Table 6, Step 4). The C-ase-1 was purified by first washing this column with Tris-DTT and Tris-DTT containing 0.10M NaCl, then eluting the C-ase-1 with Tris-DTT containing 0.11M NaCl (FIG. 2). The C-ase-1 activity recovered was still greater than that initially extracted, i.e. 22 micrograms (Table 6, Step 5). The final wash with 1M NaCl resulted in the elution of only another 1-2% of the original activity.

The eluates with C-ase-1 activity were pooled, and following concentration on the Diaflo HF-30, were incubated with anti-HSA coupled to Staph A-Sepharose (Table 6, Step 6). The resulting fraction contained approximately 21 micrograms of purified C-ase-1 activity, as determined by Lowry protein measurements against an HSA standard (Table 6, Step 6). Thus, it was estimated that in the GnRH-RIA, 15 micrograms of highly purified C-ase-1 would result in approximately 1.2 ng of apparent irGnRH. Further HPLC purification of the fractions yielded 18 micrograms of apparent irGnRH (Table 6, Step 7). A flow chart for this purification scheme and the relative specific activities at each of steps 1-7 is given in Table 6.

The highly purified C-ase-1 migrated as a single protein band ($R_f$=0.22) during PAGE, using 10% polyacrylamide gels and 0.1% SDS. When compared to standard proteins, a molecular weight of about 58,000 was estimated.

TABLE 6

| Flow Chart for Purification of C-ase-1 | | | |
|---|---|---|---|
| | C-ase-1 Activity | Protein | Specific Activity |
| Step 1 | | | |
| Fresh Lyophilized Term Placenta | microgram | milligram | microgram/ milligram |
| 2 × Acetone Precipitate | 21 | 88,000 | 0.00025 |
| Step 2 | | | |
| Tris-DTT-pepstatin buffer (300 ml) PO4 Centrifugation Supernatant (160 ml) | 18 | 7,300 | 0.0011 |
| Step 3 | | | |
| Sephadex G-150 Pool and Concentrate (Diaflo HF-30) - approx. 60,000 mol wt Eluate Blue Sepharose Filtration | 24 | 3,500 | 0.0069 |
| Step 4 | | | |
| Post Blue-Sepharose Eluate DEAE-Sepharose Column | 24 | 1,900 | 0.013 |
| Step 5 | | | |
| Pool and Concentrate (Diaflo HF-30) | 22 | 25 | 0.88 |

TABLE 6-continued

| Flow Chart for Purification of C-ase-1 | | | |
|---|---|---|---|
| | C-ase-1 Activity | Protein | Specific Activity |
| 0.10M Eluate | | | |
| Step 6 | | | |
| Anti-HSA coupled to incubate with Staph A-Sepharose PAS-DROS Pool | 21 | 21 | 1.00 |
| Step 7 | | | |
| HPLC C-ase-1 | 18 | 15 | 1.20 |

EXAMPLE 12

GnRH Bioactivity--Effect of Chorionic Peptidase 1

The effect of C-ase-1 on the GnRH-stimulated LH and FSH release in castrated rats inhibited the GnRH stimulation of LH and FSH, in a dose-related manner. A 50% inhibition of the GnRH-stimulated LH release was effected with 3.4 microgram of C-ase-1 per animal. At the 17 microgram dose, inhibition of LH below basal release was observed, suggesting that the C-ase-1 could also degrade endogenous GnRH. The FSH release stimulated by 500 ng of exogenous GnRH was inhibited 50% by as little as 3.0 microgram of C-ase-1. Basal release of FSH was also inhibited with $\geq$ 10 micrograms of C-ase-1 (See FIG. 11).

EXAMPLE 13

Use of a C-ase-1 Isolate to Affect a state of Pregnancy

Isolated C-ase-1 peptidase may be injected intraamniotically (83 micrograms in 5 ml of 10 mM Hepes, 1 mM DTT, pH 7.4) into a pregnant animal at various stages of gestation. The standard dose to an average pregnant human female would be between 70 ug and 90 ug micrograms. Such dose would be expected to induce labor in a treated pregnant animal.

EXAMPLE 14

Production of Hybridoma Secreting a Polyclonal Antibody Specific for C-ase-1 Peptide Balb/c mice were immunized by intraperitoneal administration (ea. 100 mg each) of C-ase-1 peptidase isolate by a standard dosage schedule. Mouse spleen cells were hybridized with P3K myeloma cells to form hybrid cells. The hybrid cells were plated and grown in HAT media.

EXAMPLE 15

Use of C-ase-1 in a Biological Fluid Screening Assay

The levels of C-ase-1 in biological fluids, i.e., blood, amniotic fluid, may be used to evaluate the hormonal function of pregnancy and predict its outcome. Such information may indicate therapeutic treatment to effect normal levels and this appropriate regulate hormonal levels, leading to a better outcome of the pregnancy.

The above examples report the purification of a protein from the human placenta that inactivates GnRH, TRH and angiotensin II, and is herein called chorionic peptidase-1, C-ase-1. This C-ase-1 appears to have a molecular weight of approximately 58,000 daltons as determined by Diaflo filtration. Sephadex and HPLC permeation chromatography and SDS-PAGE analyses.

It behaves as a single polypeptide chain possibly having an SH active-site, since it is stabilized by DTT, and is inactivated by trypsin. This protein does not appear to be membrane associated, since it does not precipitate in the membrane fraction with differential centrifugation. In addition, incubation studies demonstrate that it does not merely bind GnRH. However, the data suggest that C-ase-1 activity is dependent on its tertiary structure since its activity is stabilized by DTT and destroyed by guanidine, urea, heating or exposure to acid.

The hypothesis that this protein acts on GnRH, TRH and angiotensin II by a degradative enzymatic process is supported by the Applicants' demonstration that its activity on these peptides is inhibited by various enzyme inhibitors (i.e., bacitracin, para-aminobenzamidine). The action of C-ase-1 is not similar to that of trypsin or chymotrysin, since potent inhibitors of these enzymes were without effect on the C-ase-1 activity. In addition, studies of its effect on other placental peptides (hCG, hCS, CRF, OXY, SRIF) demonstrated its activity is specific for GnRH, TRH and angiotensin II. It is noteworthy that these peptides, GnRH, TRH and angiotensin II all contain proline and post-proline peptidases which are bacitracin sensitive (Griffiths, 1979; Hersh, 1979). The requirement of a basic amino acid prior to the PRO residue may result in the stability of oxytocin in its disulfide form. The precise mode of degradation of GnRH by C-ase-1 and its enzymatic kinetics have been shown.

Hypothalamic, pituitary and serum enzymes that degrade GnRH and TRH (McKelvy et al., 1976; Chertow, 1981; Kizer et al., 1986) have been reported. C-ase-1 differs from the pituitary GnRH degrading enzyme, since it is not inhibited by DTT and EDTA (Kizer et al., 1986). In addition, Applicants, data indicate that this C-ase-1 differs from blood GnRHase since it is not inhibited by EDTA (Chertow, 1981). One hypothalamic enzyme that has been described is a post-proline peptidase which degrades GnRH and TRH, but it differs from C-ase-1 in its molecular size (Hersh, 1979). Placental peptidase and acrylase activities have been described (Lampelo & Vanha-Perttula, 1980), but not purified or characterized as to activity or releasing activities. Although their activity on GnRH has not been studied, C-ase-1 differs significantly from them in specificity and molecular size. A placental deamidase activity for TRH has been reported by Nogimori et al. (1985), however, characterization of the enzyme responsible was not done. A post-proline peptidase from human placenta has also been reported, yet its molecular size and specificity differ from this C-ase-1 (Mizutani et al., 1984). Final comparison of this C-ase-1 to other placental and hypothalamic peptidases awaits their amino acid and sequence analysis.

However, it is certainly now well established that the human placenta synthesizes many peptide hormones and these peptides regulate placental function. Thus, factors such as C-ase-1 which affect the concentration of peptides like GnRH, TRH and angiotensin II may be of significance to the regulation of placental hormonogenesis.

What is claimed is:

1. An about 10,000–40,000 fold purified chorionic peptidase-1 having a molecular weight of between 50,000 to 70,000 daltons isolatable from placental tissue which enzymatically cleaves GnRH with a $K_M$ of about 4.3 $\mu$M, wherein said GnRH enzymatic activity is reduced by trypsin or at a pH of 6.5 and is not inhibited by EDTA.

2. The purified chorionic peptidase-1 of claim 1 further defined as inactivating the bioactivity and immunoreactivity of GnRH, angiotensin II and TRH.

3. An about 30,000–40,000-fold purified trypsin sensitive chorionic peptidase-1 having a molecular weight of about 58,000 daltons which cleaves GnRH with a $K_M$ of about 4.3 $\mu$M, wherein said GnRH enzymatic activity is reduced by trypsin or at a pH of 6.5 and is not inhibited by EDTA.

4. An about 40,000-fold purified chorionic peptidase-1 that degrades GnRH with a $K_M$ of about 4.3 $\mu$M and has an apparent molecular weight of between about 55,000 daltons and about 65,000 daltons which cleaves GnRH at a carboxyl end proline amino acid residue of the peptide, wherein said GnRH cleaving activity is reduced in the presence of trypsin or at a pH of 6.5 and is not inhibited by EDTA.

5. An about 30,00–40,000 fold purified chorionic peptidase-1 from placental tissue with a molecular weight between about 55,000 and 65,000 daltons that activates the bioactivity and immunoactivity of GnRH, angiotensin II and TRH, and which inactivation is reduced by trypsin or at a pH of 6.5 and is not inhibited by EDTA.

6. The purified chorionic peptidase-1 of claim 5 with an apparent molecular weight of about 58,000 daltons.

7. The chorionic peptidase-1 of claim 1 or 5 further defined as a stimulant of human chorionic gonadotrophin prostraglandis from human term placental cultures.

8. The chorionic peptidasse-1 of claim 1 or 5 which catalyses the degradation of THR, GnRH and angiotensin II.

9. The chorionic peptidase-1 of claim 1 or 3 which is inactivated at a pH below pH 6.0 or above a temperature of 60° C.

10. The chorionic peptidase-1 of claim 1 or 5 defined further as catalyzing site-specific degradation of peptides at other than disulfide bonds.

11. The chorionic peptidase-1 of claim 1 or 5 defined further as cleaving a proline carboxyl group peptide bond in a GnRH peptide sequence.

12. A placental chorionic peptidase-1 preparation for affecting the state of pregnancy in an animal, the preparation comprising a pharmaceutically acceptable carrier and a >90% purified isolate of chorionic peptidase-1 enzyme having a molecular weight of about 58,000 daltons, said chorionic peptidase-1 being capable of cleaving GnRH with a $K_M$ of about 4.3 $\mu$M, and said cleaving being reduced in the presence of trypsin or at pH of 6.5 and is not inhibited by EDTA.

* * * * *

UNITED STATES PATENT AND TRADEMARK OFFICE
CERTIFICATE OF CORRECTION

PATENT NO. : 5,168,061
DATED : December 1, 1992
INVENTOR(S) : Theresa M. Siler-Khodr It is certified that error appears in the above-indentified patent and that said Letters Patent is hereby corrected as shown below:

In claim 1 at column 18, line 6, delete "to" and insert --and--.

In claim 5 at column 18, line 30, delete "activates" and insert --inactivates--.

In claim 7 at column 18, line 38, delete "prostraglandis" and insert --prostaglandins--.

In claim 8 at column 18, line 40, delete "peptidasse-1" and insert --peptidase-1--.

Signed and Sealed this

Sixteenth Day of November, 1993

Attest:

BRUCE LEHMAN

Attesting Officer

Commissioner of Patents and Trademarks